(12) United States Patent  
Claussner et al.

(10) Patent No.: US 6,596,885 B2  
(45) Date of Patent: *Jul. 22, 2003

(54) 19-NOR STEROIDS HAVING A THIOCARBONATED CHAIN IN POSITION 11BETA, THEIR PREPARATION PROCESS AND THE INTERMEDIATES OF THIS PROCESS, THEIR USE AS MEDICAMENTS AND COMPOSITIONS

(75) Inventors: Andre Claussner, Villemomble (FR); Francois Nique, Pavillons-Sous-Bois (FR); Jean-Georges Teutsch, Pantin (FR); Patrick Van de Velde, Paris (FR)

(73) Assignee: Aventis Pharma S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/891,433

(22) Filed: Jun. 26, 2001

(65) Prior Publication Data

US 2002/0072624 A1 Jun. 13, 2002

Related U.S. Application Data

(62) Division of application No. 08/244,735, filed as application No. PCT/FR92/15856 on Dec. 17, 1992, now Pat. No. 6,281,204.

(30) Foreign Application Priority Data

Dec. 20, 1991 (FR) .............................. 91 15856

(51) Int. Cl.$^7$ .............................. C07J 1/00; C07J 31/00; C07J 41/00; A61K 31/56
(52) U.S. Cl. ...................... 552/626; 514/169; 514/177; 514/178; 514/179; 514/182; 540/2; 540/106; 540/120; 552/502; 552/515; 552/518; 552/519; 552/526; 552/531; 552/610; 552/611; 552/623; 552/625; 552/650
(58) Field of Search .................. 514/174, 175, 514/176, 179, 182, 169, 177, 178; 540/106, 108, 113, 115, 116, 120, 2; 552/518, 519, 531, 611, 626, 502, 515, 526, 610, 623, 625, 690

(56) References Cited

U.S. PATENT DOCUMENTS 6,281,204 B1 * 8/2001 Claussner et al. .......... 514/174

OTHER PUBLICATIONS

Hanson et al., "Synthesis and Estrogen Receptor Binding of Novel 11Beta–Substituted Estra–1,3,5(10)–triene–3,17Beta–diols", J. Med. Chem. (1990), vol. 33, No. 12, pp. 3155–3160.*

Napolitano et al., "Synthesis of 1, 11Beta–ethanoestra–1,3, 5(10)–triene–3,17Beta–diol: a Novel Bridged Steroid Derivative":, J. Chem. Soc., Chem. Commun. (1989), vol. 18, pp. 1330–1331.*

* cited by examiner

Primary Examiner—José G. Dees  
Assistant Examiner—Frank Choi  
(74) Attorney, Agent, or Firm—Muserlian, Lucas and Mercanti

(57) ABSTRACT

Novel compounds having a formula selected from the group consisting of

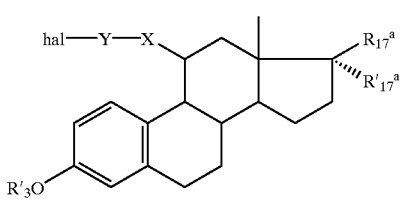

II

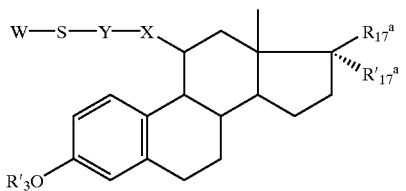

V wherein the substituents are defined as in the specification which are intermediates for the production of vinyl compounds having a remarkable anti-estrogenic and anti-proliferative activity.

1 Claim, No Drawings

19-NOR STEROIDS HAVING A THIOCARBONATED CHAIN IN POSITION 11BETA, THEIR PREPARATION PROCESS AND THE INTERMEDIATES OF THIS PROCESS, THEIR USE AS MEDICAMENTS AND COMPOSITIONS

PRIOR APPLICATIONS

This application is a division of U.S. patent application Ser. No. 08/244,735 filed Jun. 9, 1994, now U.S. Pat. No. 6,281,204, which is a 371 of PCT/FR92/15856 filed Dec. 17, 1992.

The present invention relates to new 19-Nor steroids having a thiocarbonated chain in position 11beta, their preparation process and the intermediates of this process, their use as medicaments and the pharmaceutical compositions containing them.

A subject of the invention is the compounds of formula (I):

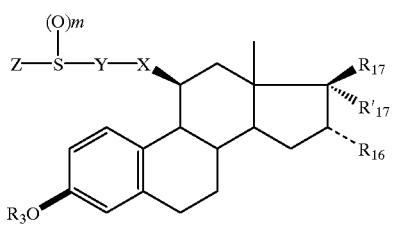

in which $R_{17}$ and $R'_{17}$ are such that:
either $R_{17}$ and $R'_{17}$ together form a ketone function, an oxime function, a hydrazono function or a methylene radical,
or $R_{17}$ is a hydroxyl radical, a hydroxymethyl radical or an acyloxy radical having at most 12 carbon atoms and $R'_{17}$ represents a hydrogen atom, an alkyl, alkenyl or alkynyl radical having at most 8 carbon atoms, each of these substituents being optionally substituted,
$R_3$ represents a hydrogen atom, a linear or branched alkyl radical or a cyclic alkyl radical having at most 8 carbon atoms or an acyl radical having at most 12 carbon atoms,
$R_{16}$ represents a hydrogen atom, a halogen atom or an alkyl radical having at most 8 carbon atoms, m has the value 0, 1 or 2, X, Y and Z are such that:
X represents a methylene radical, an arylene or arylenoxy group, having at most 10 carbon atoms linked to the steroid by a carbon atom,
Y represents a saturated or unsaturated, linear or branched aliphatic chain, containing 1 to 18 carbon atoms, optionally interrupted by an oxygen atom,
Z represents:
a linear or branched alkyl radical, containing 1 to 8 carbon atoms and optionally substituted, or an aryl or arylalkyl radical, each of these radicals being optionally substituted, in which the alkyl radical contains at most 6 carbon atoms and the aryl radical represents a monocyclic radical containing 5 or 6 members or a radical constituted by condensed rings containing 8 to 10 members, these radicals optionally containing one or more heteroatoms chosen from oxygen, nitrogen or sulphur atoms,
the alkyl radicals that can be represented by $R'_{17}$ and Z, the alkenyl or alkynyl radicals that can be represented by $R'_{17}$ and the aryl or arylalkyl radicals that can be represented by Z being optionally substituted by one or more radicals chosen from the following radicals:
halogens,
amino, alkylamino or dialkylamino in which the alkyl radical or radicals have 1 to 4 carbon atoms,
hydroxyl,
free, esterified or salified carboxy,
alkyl having 1 to 8 carbon atoms, optionally substituted by one or more halogen atoms,
oxo, cyano, nitro, formyl,
acyl or acyloxy having at most 12 carbon atoms,
alkoxy or alkylthio having 1 to 4 carbon atoms,
carbamoyl,
alkenyl or alkynyl having at most 4 carbon atoms,
aryl as defined above, and the addition salts of the above.

By acyloxy radical can be meant in particular the derivative of a saturated or unsaturated aliphatic or cycloaliphatic acid and notably an alkanoic acid such as, for example, acetic, propionic, butyric or isobutyric, valeric or undecylic acid, a hydroxyalkanoic acid such as, for example, hydroxyacetic acid; a cycloalkylcarboxylic or cycloalkylalkanoic acid such as, for example, cyclopropyl, cyclopentyl or cyclohexylcarboxylic, cyclopentyl or cyclohexyl acetic or propionic acid, a benzoic acid, a salicylic acid or a phenylalkanoic acid such as phenyl acetic or phenyl propionic acid, an amino acid such as diethylamino acetic or aspartic acid, formic acid or an optionally salified diacid, such as, for example, butanedioic acid or the monosodium salt of the latter. It is preferably the derivative of acetic, propionic or butyric acid.

By acyl radical is meant the radicals corresponding to the previous acyloxy radicals.

By alkyl radical can be meant one of the following radicals: methyl, ethyl, propyl, isopropyl, butyl, isobutyl, n-pentyl, n-hexyl, 2-methyl pentyl, 2,3-dimethyl butyl, n-heptyl, 2-methyl hexyl, 2,2-dimethyl pentyl, 3,3-dimethyl pentyl, 3-ethylpentyl, n-octyl, 2,2-dimethylhexyl, 3,3-dimethylhexyl, 3-methyl 3-ethyl pentyl.

It is preferably the methyl radical.

When $R_3$ represents a cyclic alkyl radical, it can be a cyclopropyl, cyclobutyl, cyclopentyl or cyclohexyl radical. It is preferably the cyclopentyl radical.

By alkoxy radical, can notably be meant the methoxy, ethoxy, propyloxy, butyloxy radical and by alkylthio radical, can notably be meant the methylthio, ethylthio, propylthio or butylthio radicals.

By alkenyl radical, can be meant a vinyl, propenyl, isopropenyl, allyl, 2-methyl allyl, butenyl or isobutenyl radical. It is preferably the vinyl or propenyl radical.

By alkynyl radical, can be meant the ethynyl, propynyl, propargyl, butynyl or isobutynyl radical. It is preferably the ethynyl or propynyl radical.

When $R_{16}$ represents a halogen atom, it can be a bromine, chlorine, fluorine or iodine atom; it is preferably a bromine atom.

When X represents an arylene group, it is preferably the phenylene radical.

When X represents an arylenoxy group, it is preferably the phenylenoxy radical.

When Y represents a saturated or unsaturated, linear or branched aliphatic chain, it can be one of the following radicals: methylene, ethylene, propylene, isopropylene, butylene, isobutylene, or tert-butylene, n-pentylene, n-hexylene, 2-methyl pentylene, 2,3-dimethyl butylene, n-heptylene, 2-methyl hexylene, 2,2-dimethyl pentylene, 3,3-dimethyl pentylene, 3-ethyl-pentylene, n-octylene, 2,2-dimethyl hexylene, 3,3-dimethyl hexylene, 3-methyl 3-ethyl pentylene, nonylene, 2,4-dimethyl heptylene, n-decylene, n-undecylene, n-dodecylene, n-tridecylene, n-tetradecylene, n-pentadecylene, n-hexadecylene, n-heptadecylene or n-octadecylene, preferably n-pentylene, n-hexylene, n-heptylene, n-octylene or n-nonylene.

It can also be vinylene, isopropenylene, allylene, 2-methyl allylene, isobutenylene, butenylene, pentenylene, hexenylene, heptenylene or octenylene radicals, preferably the hexenylene radical.

It can also be ethynylene, propynylene, propargenylene, butynylene, isobutynylene, pentynylene, hexynylene, heptynylene or octynylene radicals, preferably the propynylene, hexynylene or octynylene radicals.

It can be a chain interrupted by an oxygen atom, for example, an oxapolymethylene radical, preferably the oxy diethylene radical.

When Z represents a linear or branched alkyl radical, it can be the radicals indicated above, preferably propyl, butyl, n-pentyl.

When Z represents an arylalkyl group, the alkyl radical can be one of the radicals defined above, notably a methyl, ethyl, propyl, isopropyl, butyl, isobutyl, n-pentyl or n-hexyl radical, it is preferably the methyl or ethyl radical.

By aryl group which can be contained in an arylalkyl group, is meant:
- a carbocyclic monocyclic radical, for example the phenyl radical,
- a heterocyclic monocyclic radical, for example the following radicals: thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl, as well as the isomers of position of the heteroatom or heteroatoms that these radicals can contain,
- a radical constituted by carbocyclic condensed rings, for example, the naphthyl radical or phenanthrenyl radical,
- a radical constituted by heterocyclic condensed rings, for example, benzofurannyl, benzothienyl, benzimidazolyl, benzothiazolyl, naphtho[2,3-b]thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also the condensed polycyclic systems constituted by heterocyclic monocyclics, as defined, for example, above, such as for example furo[2,3-b]pyrrole or thieno[2,3-b]furan.

When Z represents an aryl or arylalkyl group, there can be mentioned as examples of such an aryl radical, in particular, the following radicals: phenyl, furyl such as 2-furyl, imidazolyl such as 2-imidazolyl, pyridyl such as 2-pyridyl, 3-pyridyl or 4-pyridyl, pyrimidinyl such as pyrimid-2-yl, thiazolyl such as thiazol-2-yl, thiazolinyl such as thiazolin-2-yl, triazolyl such as triazol-2-yl, tetrazolyl such as tetrazol-2-yl, benzimidazolyl such as benzimidazol-2-yl, benzothiazolyl such as benzothiazol-2-yl, purinyl such as purin-7-yl or quinolyl such as 4-quinolyl and as examples of arylalkyl radicals, there can also be mentioned in particular the methyl or ethyl radicals substituted by one of the above aryl radicals.

The expression optionally substituted applied to the alkyl radicals that can be represented by $R'_{17}$ and Z, the alkenyl or alkynyl radicals that can be represented by $R'_{17}$ and the aryl or arylalkyl radicals that can be represented by Z, indicates that these can be optionally substituted by one or more identical or different radicals chosen from the radicals indicated previously and in particular, halogen: fluorine, chlorine, bromine, iodine, amino, alkylamino such as methylamino or ethylamino, dialkylamino such as dimethylamino, diethylamino, methylethylamino, hydroxyl, free, esterified carboxy such as alkoxy carbonyl for example methoxy carbonyl or ethoxycarbonyl, or carboxy salified for example by a sodium or potassium atom, alkyl having 1 to 8 carbon atoms such as methyl, ethyl, propyl, isopropyl, butyl, isobutyl, tert-butyl, optionally substituted by one or more halogen atoms, for example fluorine such as trifluoromethyl, oxo, cyano, nitro, formyl, acyl such as acetyl, propionyl, butyryl, benzoyl, acyloxy such as acetoxy, a radical of formula —O—CO—$(CH_2)_n$—COOH in which n=1 to 5, alkoxy such as methoxy, ethoxy, propyloxy, isopropyloxy, butyloxy, alkylthio such as methylthio, ethylthio, propylthio, isopropylthio, butylthio, carbamoyl, alkenyl such as vinyl, propenyl, alkynyl such as ethynyl, propynyl, aryl such as phenyl, furyl, thienyl.

As an example of such substituted radicals, there can be mentioned for example an alkyl radical substituted by one or more halogen atoms, for example, fluorine, such as the trifluoroethyl, trifluorobutyl, pentafluoropropyl, pentafluorobutyl, pentafluoropentyl, heptafluorobutyl or nonafluorobutyl radical, an alkyl radical substituted by an aryl radical, for example the phenyl radical, itself substituted by one or more halogen atoms and/or alkyl radicals substituted by one or more halogen atoms, such as pentafluorobenzyl, pentafluorophenylethyl, pentafluorophenylpropyl, 4-trifluoromethyl 2,3,5,6-tetrafluorobenzyl.

There can also be mentioned, for example, an aryl radical substituted by one or more halogen atoms, for example, chlorine such as 2,3,5,6-tetrachloro 4-pyridyl, by an amino group such as 4,6-diamino 2-pyrimidinyl, by a hydroxyl such as 2,6-dihydroxy 4-pyrimidinyl, by an esterified carboxyl for example a methoxycarbonyl such as 2-methoxycarbonyl phenyl, by an alkyl, for example a methyl such as N-methyl imidazolyl, N-methyl triazolyl or N-methyl tetrazolyl, optionally substituted by a halogen for example fluorine such as 7-(trifluoromethyl) 4-quinolyl, by an oxo group and an alkyl radical, for example, a methyl radical such as 1,3-dimethyl 2,6-dioxopurin-7-yl.

The invention naturally extends to the salts of the compounds of formula (I), such as for example, the salts formed when the compounds of formula (I) contain an amino function, with the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkanesulphonic, such as methane or ethanesulphonic, arenesulphonic, such as benzene or paratoluene sulphonic and arylcarboxylic, or when the compounds of formula (I) contain an acid function, with the salts of alkali or alkaline-earth metals or of optionally substituted ammonium.

Among the preferred compounds of formula (I) of the invention, there can be mentioned in particular the compounds in which $R_3$ and $R_{16}$ represent a hydrogen atom.

Among the preferred compounds of formula (I) of the invention, the compounds in which m=1 and those in which m=2 can be particularly mentioned.

Among the compounds of the invention, there can be mentioned in particular the compounds of formula (I), in which $R_{17}$ is a hydroxyl radical and $R'_{17}$ is a hydrogen atom or a methyl radical.

Among the compounds of the invention, there can be mentioned in particular the compounds of formula (I), in which X represents a methylene radical and Y is a saturated linear chain containing 7 to 9 carbon atoms, those in which X represents a phenylene radical and Y represents a saturated or unsaturated linear chain containing 3 to 8 carbon atoms, it being understood that, when the chain is unsaturated, it contains a vinylene or ethynylene group linked directly to the phenylene radical and those in which X represents a phenylenoxy radical and Y represents a saturated linear chain containing 4 to 7 carbon atoms, optionally interrupted by an oxygen atom. When X represents a phenylenoxy radical, Y preferably contains 5 or 6 carbon atoms.

Among the compounds of the invention, there can be mentioned especially the compounds of formula (I) in which Z represents a linear alkyl radical containing 1 to 5 carbon atoms, a trifluoroalkyl radical containing 2 to 4 carbon atoms, a pentafluoroalkyl radical containing 4 or 5 carbon atoms, a nonafluoroalkyl radical containing 1 to 4 carbon atoms, a radical containing a substituted phenyl radical chosen from:

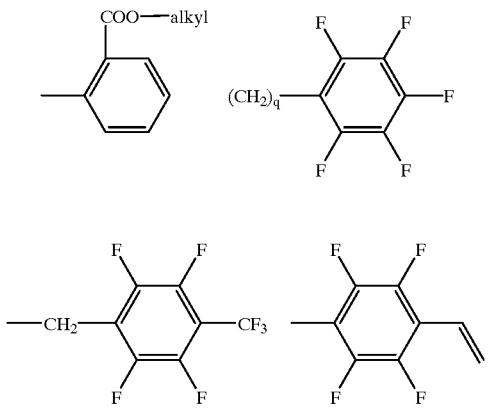

in which the alkyl represents an alkyl radical containing 1 to 4 carbon atoms and q represents the values 1, 2 or 3.

a radical containing a heterocycle with 5 members chosen from:

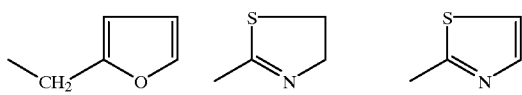

a radical containing a heterocycle with 6 members chosen from:

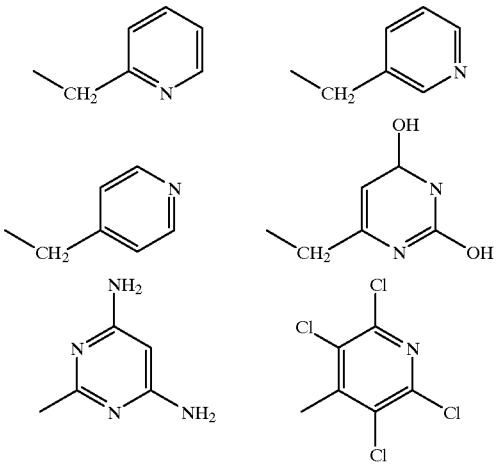

a radical containing a heterocycle with two condensed rings chosen from:

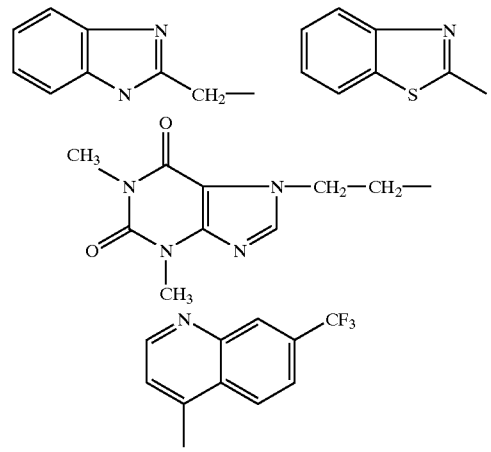

Among the preferred values of Z, there can be mentioned more particularly the pentyl value and the pentafluoroalkyl value and in particular the pentafluoropropyl, pentafluorobutyl or pentafluoropentyl values.

Therefore, among the preferred compounds of the invention, there can be mentioned the compounds whose preparation is given hereafter in the experimental part and more particularly:

11beta-[-8-[(2-pyridinylmethyl)thio]octyl]estra-1,3,5(10)-triene-3,17beta-diol,
11beta-[4-[3-[(1-methyl 1H-imidazol-2-yl)thio]1-propynyl]phenyl]estra-1,3,5(10)-triene-3,17beta-diol,
11beta-[4-[5-[(2-furanylmethyl)thio]pentyloxy]phenyl]estra-1,3,5(10)-triene-3,17beta-diol,
11beta-[4-[5-[(2-pyridinylmethyl)sulphinyl]pentyloxy]phenyl]estra-1,3,5(10)-triene-3,17beta-diol, 11beta-[4-[5-[(3-pyridinylmethyl)sulphinyl]pentyloxy] phenyl]estra-1,3,5(10)-triene-3,17beta-diol, 11beta-[4-[6-[(4,4,5,5,5-pentafluoro pentyl)sulphinyl] hexyloxy]phenyl]estra-1,3,5(10)-triene-3,17beta-diol, 11beta-[4-[5-[(4,4,5,5,5-pentafluoropentyl)sulphinyl] pentyloxy]phenyl]estra-1,3,5(10)-triene-3,17beta-diol, 11beta-[4-[5-(pentylsulphonyl)pentyloxy]phenyl]estra-1,3,5(10)-triene-3,17beta-diol, 11beta-[4-[5-[(4,4,5,5,5-pentafluoro pentyl)sulphonyl] pentyloxy]phenyl]17alpha-methyl estra-1,3,5(10)-triene-3,17beta-diol.

Also a subject of the invention is a preparation process for the compounds of formula (I) characterized in that a compound of formula (II):

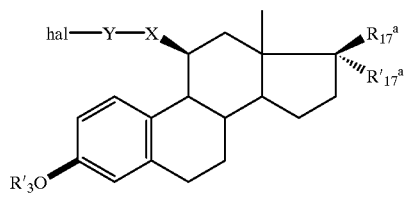

(II)

in which:
- $R_{17a}$ and $R'_{17a}$ have the meanings indicated previously for $R_{17}$ and $R'_{17}$ and in which the optional reactive functions are optionally protected,
- X and Y have the same meaning as previously,
- $R'_3$ represents a hydrogen atom or a protective group of the hydroxyl function,
- hal represents a halogen atom or a pseudo-halogen group such as a tosylate, is subjected to the action of a mercaptan of formula (III):

Za—SH (III)

or a salt of the latter, in which Za has the meaning indicated previously for Z in which the optional reactive functions are optionally protected, then, if appropriate, to the action of an elimination agent of the protective groups, in order to obtain the compound of formula (IA) corresponding to the product of formula (I) in which m=0, which product of formula (IA) is subjected, if desired and if necessary, to any one of the following reactions, in any order:

reduction of the ketone function which can be represented by $R_{17}$ and $R'_{17}$ together, addition on the ketone function which can be represented by $R_{17}$ and $R'_{17}$ of a metallic complex of formula (IV):

M-$R'_{17a}$ (IV)

in which M represents a metal atom and $R'_{17a}$ has the same meaning as previously, it being understood that it is not a hydrogen atom, conversion of the ketone function which can be represented by $R_{17}$ and $R'_{17}$ together into an oxime function, into a hydrazono or methylene group, selective acylation in position 17 when $R_{17}$ is a hydroxyl, halogenation or alkylation in position 16, alkylation or acylation of the hydroxyl radical in position 3, partial or total reduction of the ethynylene group, when Y represents an unsaturated chain, oxidation of the sulphur into the sulphoxide or sulphone, optional salification by an acid or a base.

The compounds of formula (IA) corresponding to the compounds of formula (I) in which m=0, are obtained by reacting a compound of formula (II), in which hal is for example a chlorine atom, a bromine atom or a tosylate, $OR_3$ is a hydroxyl optionally protected for example by an acetyl, tertiobutyl or tetrahydropyranyl radical and $R_{17a}$ $R'_{17a}$ have reactive functions optionally protected by the usual methods, with a compound of formula (III), preferably in the form of a salt obtained by the addition, for example, of sodium carbonate, soda or sodium methylate or ethylate, the reaction being carried out in a neutral solvent, for example methanol, dimethylformamide, hexamethylphosphorotriamide (HMPT) or acetonitrile ($CH_3CN$), by itself or in a mixture, operating, for example, at approximately 50° C. or under reflux, if necessary in the presence of a reagent such as sodium iodide, then if appropriate, subjecting the compound obtained to the action of a deprotection agent of the reactive functions.

According to the values of the protective group $R'_3$, the products of formula ($I_A$) can represent products of formula (I).

The protective groups which can be used to protect the reactive functions, such as, for example, the amino or hydroxyl functions, are chosen from the usual groups from organic chemistry and more particularly from the chemistry of the peptides. A non-exhaustive list of these groups as well as the corresponding elimination methods can be found in the French Patent FR 2,499,995 whose content is incorporated in the present Application by way of reference. For example, the tetrahydropyrannyl or trityl radicals can be mentioned.

In a preferred embodiment of the invention:

the compounds of formula (II) containing a chain in position 11beta terminated by a halogen or a pseudohalogen such as, for example, the group —O—$SO_2$—Φ—$CH_3$ in which Φ represents a phenylene radical, as illustrated in the following examples, as well as the compounds of formula (III) mentioned below in the experimental part, can be used. In a non-exhaustive manner, the following can be mentioned: the methyl ester of 2-mercapto benzoic acid, furfurylmercaptan, 2-thiazoline-2-thiol, 2-mercapto thiazole, 2-mercapto 1-methyl imidazole, 1-methyl 5-mercapto-1,3,4-thiazole, 1-methyl 5-mercapto 1,2,3, 4-tetrazole, 2-pyridinemethanethiol, 4,6-diamino pyrimidine-3-thiol, 2,3,5,6-tetrachloro pyridine-4-thiol, 2-mercapto benzothiazole, 7-trifluoromethyl 4-quinolinethiol and 4,4,5,5,5-pentafluoropentanethiol.

When the compound of formula (IA) contains protected reactive functions, the corresponding deprotected compound is obtained by the action of standard agents, for example, a saponification agent such as potash in an alcoholic medium or a hydrolysis agent such as hydrochloric acid. The deprotection methods which can be used are also described in the French Patent FR 2,499,995.

When the compound of formula (IA) contains a ketone function in position 17:

the corresponding hydroxylated 17beta compound is obtained for example by the action of a reducing agent such as sodium borohydride in a neutral solvent such as methanol, the corresponding compound containing an $R'_{17}$ radical representing an optionally substituted alkyl, alkenyl or alkynyl radical is obtained, by the addition of a compound (IV), such as, for example, a lithium complex, according to the process described in the European Patent EP 57115, the corresponding compound containing an oxime function in position 17 is obtained, for example, by the action of hydroxylamine in the form of a salt such as the hydrochloride, in the presence of a weak base in an alcohol at reflux temperature, the corresponding compound containing a hydrazono function in position 17 is obtained, for example by the action of a derivative of hydrazine and notably hydrazine hydrate in the presence of an acid such as paratoluenesulphonic acid, the corresponding compound containing a methylene function in position 17 is obtained by using a Wittig reaction, for example, methyltriphenylphosphonium bromide in a basic medium.

When the compound of formula (IA) contains a hydroxyl function in position 3 or 17, the corresponding 3 or 17beta acyloxylated compound is obtained, by the action of a selective acylation agent, for example, acetic anhydride in pyridine.

When the compound of formula (IA) contains an ethynylene group, the corresponding compound having a vinyl bond or the corresponding saturated compound is obtained by the action of a partial or total reducing agent, either by using hydrogen in the presence of palladium, on activated charcoal or over barium sulphate and optionally in the presence of a base such as pyridine or quinoline, in the case of a partial reduction, or using palladium hydroxide by itself in the case of a total reduction.

The compounds containing an alkyl radical in position 16 can be obtained, for example, by the action of an alkyl halide, such as methyl iodide or ethyl iodide in the presence of a lithium complex.

The compound containing a halogen in position 16 can be obtained, for example, by the action of bromine in an acid medium notably in acetic acid or also by the action of a halogenation agent such as N-bromo or N-chloro succinimide or N-bromo or N-chloro acetamide or also tertbutyl hypochlorite.

The compounds of formula (IA) can be subjected to a sulphoxidation agent, for example, sodium metaperiodate or metachloroperbenzoic acid in order to obtain the compounds of formula (I) in which m=1, or to a sulphonation agent, for example, perphthalic acid or metachloroperbenzoic acid in order to obtain the compounds of formula (I) in which m=2.

The invention also relates to a preparation process for the compounds of formula (I), characterized in that a compound of formula (V):

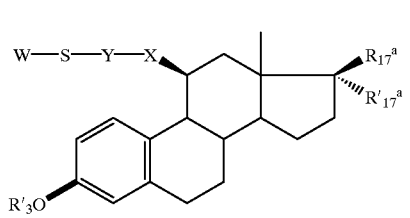

(V)

in which:
$R_{17a}$ and $R'_{17a}$ have the meanings indicated previously for $R_{17}$ and $R'_{17}$ in which the optional reactive functions are optionally protected,
X and Y have the same meaning as previously,
$R'_3$ represents a hydrogen atom or a protective group of the hydroxyl function,
W represents a hydrogen atom or an acyl —COR radical in which R represents an alkyl radical containing 1 to 5 carbon atoms, is subjected to the action of a compound of formula (VI):

Za-hal'  (VI)

or a salt of the latter, in which Za has the meaning indicated previously for Z in which the optional reactive functions are optionally protected and hal' represents a reactive group such as a halogen or a pseudohalogen such as a mesylate or tosylate group, in the presence of a base, then if appropriate to the action of an elimination agent of the protective groups in order to obtain the compound of formula (IA) as defined above and that, if desired and if necessary, is subjected to any one of the reactions indicated for the compound of formula (IA) above.

According to this variant of the process of the invention, the compounds of formula (IA) corresponding to the compounds of formula (I) in which m=0 are obtained by reacting a compound of formula (V) in which when W is an acyl group, this can be, for example, an acetyl, propionyl, butyryl radical; $OR'_3$ is a hydroxyl radical optionally protected, for example, by an acetyl, tertiobutyl or tetrahydropyrannyl radical; the reactive functions that can be contained by $R_{17a}$ and $R'_{17a}$ are optionally protected by the usual methods, with a compound of formula (VI) or a salt of the latter, for example, a hydrochloride, the reaction being carried out in a solvent such as methanol or dimethylformamide which is optionally heated, for example, to approximately 50° C. or under reflux and in the presence of a base such as sodium methylate or concentrated soda.

In a preferred embodiment of the invention:
the compounds of formula (V) containing a chain in position 11beta terminated by a thiol or thioacetyl group as well as the compounds of formula (VI) mentioned hereafter in the experimental part are used.

In a non-exhaustive manner, there can also be mentioned as compounds of formula (VI), either 3-chloromethylpyridine, 4-chloromethylpyridine, 6-(chloromethyl)uracile, 2-chloromethylbenzimidazole, 7-(2-chloroethyl)theophylline and the addition salts of the latter, such as hydrochloride, or iodopentane, or mesylate, tosylate or a pentafluoropentyl halide or trifluorobutyl preferably 4,4,5,5,5-pentafluoroiodopentane, 4,4,4-trifluoroiodobutane as illustrated in the examples hereafter.

The 4,4,5,5,5-pentafluoro iodopentane, whose preparation is described below in the experimental part, is obtained by the iodization of the corresponding alcohol, 4,4,5,5,5-fluoropentanol, the which product can be prepared, for example, by subjecting the corresponding partially unsaturated, 4,4,5,5,5-pentafluoro-2-penten-1-ol product, which is described by T. Kitazume et al., J. Am. Chem. Soc 1985, 107, 5186–5191, to a hydrogenation reaction, in the presence of a catalyst such as, for example, Raney nickel in methanol or platinum oxide in ethanol.

The above saturated intermediate alcohol can also be prepared according to a process described by N. O. Brace, Journal of Fluorine Chemistry 20 (1982), 313–327, starting from iodo-pentafluoroethane which is condensed under pressure with allyl alcohol, in the presence of a catalyst such as, for example, azaisobutyronitrile (AIBN), Raney nickel in ethanol, tetra kis (triphenylphosphino) palladium in hexane or tin and silver acetate in methanol in order to obtain 2-iodo-4,4,5,5,5-pentafluoropentanol which is subjected to a hydrogenation reaction, for example, by hydrogen in the presence of palladium with 10% magnesia in methanol or of Raney nickel in ethanol, or by reaction with tributyl tin hydride in the presence of azoisobutyronitrile.

The compounds of formula (IA) obtained according to the variant of the process are then, if necessary, subjected to one of the reactions indicated above, in order to obtain the compounds of formula (I).

The compounds of formula (I) have useful pharmacological properties. Study of the products on the hormonal receptors has revealed that they possess in particular a remarkable anti-estrogen activity and antiproliferative properties, as the results of the tests given hereafter show. They also possess an anti-nidatory activity.

These properties amke the compounds of formula (I) useful in controlling fertility, for example, in some forms of anovulatory sterility, in birth control, for example, as a contraceptive and notably as a post-coital pill, as well as in the treatment of hormonal-dependent carcinomas, such as, for example, mammary carcinomas and their metastases and in the treatment of benign tumors of the breast.

Therefore a subject of the invention is the products of formula (I) as medicaments.

Among the medicaments of the invention, the compounds described in the experimental part and especially the products of the examples can be mentioned in particular. Among these products, a particular subject of the invention is, as medicaments, the following compounds of formula (I):

11beta-[8-[(2-pyridinylmethyl)thio]octyl]estra-1,3,5(10)-triene-3,17beta-diol,

11beta-[4-[3-[(1-methyl 1H-imidazol-2-yl)thio]1-propynyl]phenyl]estra-1,3,5(10)-triene-3,17beta-diol, 11beta-[4-[5-[(2-furanylmethyl)thio]pentyloxy]phenyl]estra-1,3,5(10)-triene-3,17beta-diol, 11beta-[4-[5-[(2-pyridinylmethyl)sulphinyl]pentyloxy]phenyl]estra-1,3,5(10)-triene-3,17beta-diol, 11beta-[4-[5-[(3-pyridinylmethyl)sulphinyl]pentyloxy]phenyl]estra-1,3,5(10)-triene-3,17beta-diol, 11beta-[4-[6-[(4,4,5,5,5-pentafluoropentyl)sulphinyl]hexyloxy]phenyl]estra-1,3,5(10)-triene-3,17beta-diol, 11beta-[4-[5-[(4,4,5,5,5-pentafluoropentyl)sulphonyl]pentyloxy]phenyl]estra-1,3,5(10)-triene-3,17beta-diol, 11beta-[4-[5-(pentylsulphonyl]pentyloxy]phenyl]estra-1,3,5(10)-triene-3,17beta-diol, 11beta-[4-[5-[(4,4,5,5,5-pentafluoropentyl)sulphonyl]pentyloxy]phenyl]17alpha-methyl estra-1,3,5(10)-triene-3,17beta-diol.

The useful dose varies as a function of the illness to be treated and the administration route; it can vary, for example, from 1 to 100 mg per day in an adult by oral route.

The invention extends to pharmaceutical compositions containing at least one of the medicaments as defined above as active ingredient.

The compounds of formula (I) are used by digestive, parenteral or local route, for example, by percutaneous route. They can be prescribed in the form of plain or sugar-coated tablets, capsules, granules, suppositories, pessaries, injectable preparations, ointments, creams, gels, microbeads, implants, patches; which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

Some of the intermediates of formula (II) or (V) are new products and therefore a subject of the invention is also the compounds of formulae (II) and (V) as defined previously.

The new intermediate compounds of formula (II) as defined previously are prepared according to an operating method an example of which is given hereafter.

In a general manner, the compounds of formula (II) can be prepared according to the following process:

either a compound of formula (VII):

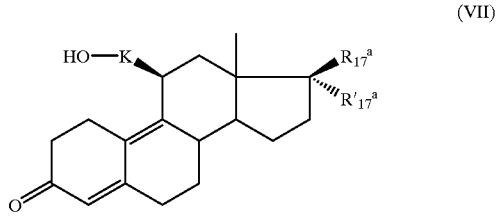

(VII)

in which $R_{17a}$ and $R'_{17a}$ have the meaning given previously, K represents an aliphatic chain containing 2 to 19 carbon atoms linked to the steroid nucleus by a methylene radical or an arylene group, is subjected, a) to the action of an activation agent of the alcohol function, for example tosyl chloride in pyridine, or to a halide-forming agent for example carbon tetrachloride or tetrabromide in the presence of triphenylphosphine in a neutral solvent, when K is an aliphatic chain, b) to the action of a halogenated compound of formula (VIII):

Br—Y-hal        (VIII)

in which Y has the meaning indicated above and hal represents a halogen, in the presence of a base, when K is an arylene group, then, in both cases, to an aromatization agent such as palladium hydroxide on magnesia in methanol or an acetyl bromide-acetic anhydride mixture, in order to obtain the compounds of formula (II) in which X represents a methylene radical and the compounds of formula (II) in which X represents an arylenoxy group respectively, or the compound of formula (VII) as defined above is subjected first, to the above aromatization reaction then to reaction a) or b) as indicated above, or a compound of formula (IX):

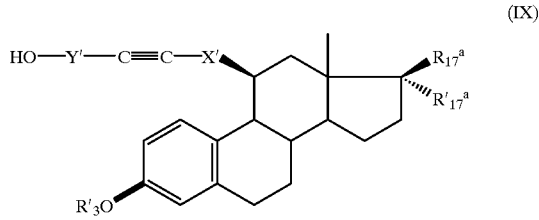

(IX)

in which $R'_3$, $R_{17a}$ and $R'_{17a}$ have the meaning given previously, X' represents an arylene group and Y' represents Y as defined above containing 2 les carbon atoms at the level of the bond with the arylene group which is represented by X', is subjected to the action of an activation agent of the alcohol function, for example, carbon tetrachloride in the presence of triphenylphosphine in a neutral solvent or tosyl chloride in pyridine, in order to obtain the compounds of formula (II) in which X is an arylene group and Y is linked directly to X by an ethynylene group, which products can be subjected, if desired, to a partial or total reaction of the triple bond.

Some of the products of formula (VII) which are necessary for the implementation of the process are known products. Their preparation is described in the preparation of the products of Example 43 and Example 50, in the European Patent Application EP 384842 the content of which is incorporated in the present Application by way of reference. The new products of formula (VII) can be prepared in a similar way, for example, by following the method described in the above Patent Application.

The products of formula (IX) which are necessary for the implementation of the process are products which are prepared according to known methods, from products of formula (X):

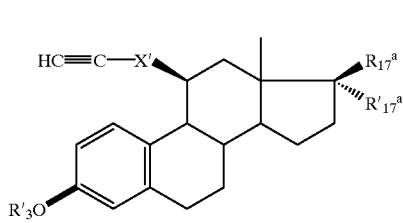

(X)

in which $R'_3$, $R_{17a}$, $R'_{17a}$ and X' have the meaning given previously.

Starting from the products of formula (X), the products of formula (IX) are obtained by reacting, for example, either paraformaldehyde in the presence of butyl and lithium chloride in a neutral solvent, when Y' represents a methylene radical, or a halide of formula Rp—O—Y'-Hal$_1$ in which Hal$_1$ is a halogen and Rp a protective group of the alcohol function in the presence of a strong base, when Y' represents an aliphatic chain having at least 2 carbon atoms. Examples of such a preparation are given hereafter in the experimental part.

Some products of formula (II), in which hal represents a halogen can also be obtained directly by reacting a halide of formula Hal$_2$—Y'-Hal$_1$ in which Hal$_1$ and Hal$_2$ respectively represent a halogen, in the presence of a strong base.

Products of formula (X) are described for example in the European Patent Application EP 384842 and other products of formula (X) can be prepared in a similar way, for example, by following the method described in the preparation of Example 31 of the above Application.

The new intermediate compounds of formula (V) as defined previously are prepared according to an operating method an example of which is given hereafter.

In a general manner, the compounds of formula (V) can be prepared according to the following process:

A compound of formula (II') corresponding to the compound of formula (II) defined above in which hal represents a chlorine or bromine atom, is subjected, either to the action of an iodation agent, for example, sodium iodide in a neutral solvent such as acetone or methylethylketone which is optionally heated under reflux, then to the action of a salt of thiocarboxylic acid of formula (XI):

R—CO—SH    (XI)

in which R has the meaning given previously, in order to obtain the compound of formula (V) in which W is an acyl radical, or to the action of the compound of formula (XI) indicated above in order to obtain the disulphide compound of formula (XII):

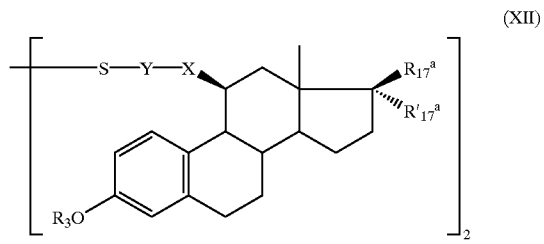

in which $R_3$, X, Y, $R_{17a}$ and $R'_{17a}$ have the meaning given previously, which is subjected to a reducing agent of the disulphide, for example, tri-n-butylphosphine in a neutral solvent such as an aqueous organic solvent in order to obtain the compound of formula (V) in which W is a hydrogen atom.

In addition to the following examples which illustrate the invention without, however, limiting it, the products of formula (I) in which $R_{17}$ represents a hydroxyl, $R'_{17}$ represents a hydrogen atom, m has the values 0, 1 or 2 and X, Y, Z have the values given in the table below, constitute products which can be obtained within the scope of the present invention:

| —X | —Y | —Z |
|---|---|---|
| —Φ | —C≡C—(CH$_2$)$_4$ | —(CH$_2$)$_3$—CF$_2$—CF$_3$ |
| —Φ | —(CH$_2$)$_6$ | —(CH$_2$)$_3$—CF$_2$—CF$_3$ |
| —ΦO | —(CH$_2$)$_4$ | —CH$_2$—CF$_2$—CF$_2$—CF$_3$ |
| —ΦO | —(CH$_2$)$_5$ | —CH$_2$—CF$_2$—CF$_2$—CF$_3$ |
| —ΦO | —(CH$_2$)$_7$ | —CH$_2$—CF$_2$—CF$_2$—CF$_3$ | in which Φ has the meaning indicated previously.

EXAMPLE 1

11beta-[8-[(2-pyridinylmethyl)thio]octyl]estra-1,3,5 (10)-triene-3,17beta-diol

Stage A: 17beta-acetyloxy 11beta-[8-(acetyloxy)octyl]estra-4,9-dien-3-one 3.6 cm$^3$ of acetic anhydride and 95 mg of 4-(dimethylamino) pyridine are added to a solution of 1.4 g of 17beta-(acetyloxy)11beta-(8-hydroxy octyl)-estra-4,9-dien-3-one (obtained by a similar process to Stage D of the preparation of Example 50 of the European Patent Application EP 384 842) in 10 cm$^3$ of pyridine. The solution is agitated for one hour at ambient temperature, 5 cm$^3$ of water and 5 cm$^3$ of methanol are added, followed by agitation for ten minutes at 0°/+5° C., the whole is poured into a saturated aqueous solution of ammonium chloride, extracted with ethyl acetate, washed with a saturated solution of sodium chloride, dried and evaporated to dryness under reduced pressure after having entrained the pyridine with toluene. 1.61 g of crude product is obtained which is chromatographed on silica, eluant: ethyl acetate-cyclohexane 3-7. In this way 1.28 g of desired product is collected.

| I.R. Spectrum: in CHCl$_3$ | |
|---|---|
| C=O | 1735 cm$^{-1}$ |
| dienone | 1660-1605 cm$^{-1}$ |

Stage B: 11beta-[8-(acetyloxy)octyl]estra-1,3,5(10)-triene-3,17beta-diol diacetate 1.273 g of the product obtained in the preceding stage is dissolved in 13 cm$^3$ of methylene chloride with 1.3 cm$^3$ of acetic anhydride and 0.65 cm$^3$ of acetyl bromide, agitation is carried out for 10 minutes at 0° C. then for 1 hour 30 minutes at ambient temperature, followed by cooling down and 2 drops of water and 3 cm$^3$ of methanol are added. The reaction medium is poured into a saturated solution of sodium bicarbonate, extracted with methylene chloride, washed with water, dried and evaporated to dryness under reduced pressure. 1.387 g of desired product is obtained.

| I.R. Spectrum: | |
| --- | --- |
| C=O | 1740-1730 cm$^{-1}$ |
| Aromatic | 1610-1590-1500 cm$^{-1}$ |

Stage C: 11beta-(8-hydroxy octyl)estra-1,3,5(10)-triene-3,17beta-diol 20 cm$^3$ of 2N soda is slowly added to a solution of 1.377 g of the product obtained in the previous stage in 42 cm$^3$ of methanol and agitation is carried out for 2 hours and 30 minutes at ambient temperature, 21.5 cm$^3$ of 2N hydrochloric acid is added then the whole is poured into a saturated solution of sodium bicarbonate, extracted with ethyl acetate, washed with water saturated with sodium chloride, dried and evaporated to dryness under reduced pressure. 1.119 g of desired product is obtained which is used as it is for the following stage.

Stage D: 11beta-(8-bromo octyl)estra-1,3,5(10)-triene-3,17beta-diol

A solution of 2.88 g of triphenyl phosphine in 8.1 cm$^3$ of methylene chloride is added dropwise to a solution of 1.107 g of the product obtained in the previous stage in 32.5 cm$^3$ of acetonitrile with 8.1 cm$^3$ of tetra-hydrofuran and 2.561 g of carbon tetrabromide at 40° C. The reaction medium is agitated for one hour at ambient temperature and evaporated to dryness under reduced pressure. 6.05 g of product is obtained which is chromatographed on silica (eluant ethyl acetate-cyclohexane 3/7). 283 mg of expected product is obtained.

| I.R. Spectrum: | |
| --- | --- |
| OH | 3605 cm$^{-1}$ |
| Aromatic | 1615-1600-1590-1500 cm$^{-1}$ |

Stage E: 11beta-[8-[(2-pyridinylmethyl)thio]octyl]estra-1,3,5(10)-triene-3,17beta-diol A mixture of 125 mg of 2-pyridine methane thiol and 0.98 cm$^3$ of a solution at 51.3 mg/cm$^3$ of sodium methylate in methanol is agitated for 5 minutes then a solution of 155 mg of the product obtained in the previous stage in 4 cm$^3$ of methanol is added at ambient temperature, 60 mg of sodium iodide is added and the whole is agitated for one hour under reflux. After cooling down, the reaction medium is poured into water, extracted with ethyl acetate, washed with water saturated with sodium chloride and evaporated to dryness under reduced pressure. 224 mg of product is collected which is chromatographed on silica (eluant methylene chloride-methanol 97.5/2.5 then again with ethyl acetate-cyclohexane 40/60).

| I.R. Spectrum: | |
| --- | --- |
| OH | 3604 cm$^{-1}$ |
| | 1616 |
| Aromatics | 1598 |
| | 1584 |
| heterocycles | 1571 |
| | 1498 |

EXAMPLE 2

11beta-[4-[3-[(1-methyl 1H-imidazol-2-yl)thio]1-propynyl]phenyl]estra-1,3,5(10)-triene-3,17beta-diol Stage A: 3,17beta-bis-(tetrahydro 2H-2-pyrannyloxy) 11beta-(4-ethynyl phenyl)estra-1,3,5(10)-triene A mixture of: 0.1 cm$^3$ of chlorobutane, 14 mg of lithium powder, 540 mg of 3-[4-[3,17beta-bis-(tetrahydro 2H-2-pyrannyloxy)estra-1,3,5(10)-trien-11beta-yl]phenyl]prop-2-yn-1-ol (obtained in Stage D of Preparation B of Example 31 of the Patent Application EP 384842) and 2 cm$^3$ of tetrahydrofuran is agitated in an ultrasound tank, agitation is carried out for thirty minutes at 30/35° C. and 29 mg of paraformaldehyde is added, agitation is carried out again for a few minutes at 30/35° C., followed by diluting with water, acidifying with monosodium phosphate, extracting with methylene chloride, drying and evaporating to dryness under reduced pressure. 613 mg of product is obtained which is chromatographed on silica (eluant cyclohexane-ethyl acetate 1/1) in this way 400 mg of desired product is collected (M.p.=214° C.).

| I.R. Spectrum: | |
| --- | --- |
| C≡CH | absence |
| OH | 3609 cm$^{-1}$ |
| aromatic | 1607-1572-1555-1492 cm$^{-1}$ |

Stage B: 3,17beta-bis-(tetrahydro 2H-2-pyrannyloxy) 11beta-[4-(3-chloro-1-propynyl)phenyl]estra-1,3,5(10)-triene A solution containing: 570 mg of the product obtained in the previous stage, 14 cm$^3$ of carbon tetrachloride, 2 cm$^3$ of tetrahydrofuran and 4 cm$^3$ of acetonitrile and finally, by portions, 530 mg of triphenyl phosphine, is agitated for 1 hour at ambient temperature and for 2 hours under reflux. 5 g of silica is added followed by evaporating to dryness under reduced pressure. The residue obtained is chromatographed on silica (eluant cyclohexane-ethyl acetate 8-2). 370 mg of desired product is collected.

| I.R. Spectrum: CHCl$_3$ on Nicolet | |
| --- | --- |
| OH | 3598 cm$^{-1}$ |
| C≡C | 2268 (f)-2220 cm$^{-1}$ |
| aromatic | 1606-1560-1531-1506 cm$^{-1}$ |

Stage C: 3,17beta-bis-(tetrahydro 2H-2-pyrannyloxy) 11beta-[4-[3-[(1-methyl 1H-imidazol-2-yl)thio]1-propynyl]phenyl]estra-1,3,5(10)-triene 38 mg of sodium hydride in 50% dispersion in oil is added to a solution cooled down to 0° C. containing 90 mg of 2-mercapto-1-methyl imidazole and 2 cm$^3$ of tetrahydrofuran. The reaction medium is agitated for 1 hour at 0° C. A solution of 2 g of the product obtained in the previous stage in 2 cm³ of tetrahydrofuran is added. The temperature is allowed to return to ambient and agitation is carried out again for 3 hours. The reaction mixture is poured into an aqueous solution of ammonium chloride, extracted with ethyl acetate, dried and evaporated to dryness under reduced pressure. The product obtained is chromatographed on silica (eluant ethyl acetate-cyclohexane 2/8). 180 mg of desired product is obtained.

| I.R. Spectrum: CHCl₃ on Nicolet | |
| --- | --- |
| OH | 3600 cm⁻¹ |
| C≡C | 2218 |

Stage D: 11beta (4(3-(methyl 1H-imidazol-2-yl)thio)1-propynyl)phenyl)estra-1,3,5(10)-triene-3,17beta-diol A mixture containing 143 mg of the product obtained in the previous stage, 2 cm³ of ethanol and 2 cm³ of 2N hydrochloric acid is agitated for 2 hours at ambient temperature. After concentrating to a reduced volume, extraction is carried out with ethyl acetate followed by evaporating to dryness under reduced pressure. The residue is chromatographed on silica (eluant cyclohexane-ethyl acetate 1/1). 96 mg of desired product is collected.

| I.R. Spectrum: CHCl₃ on Nicolet | |
| --- | --- |
| OH | 3608 cm⁻¹ + associated |
| C≡C | 2210 cm⁻¹ |
| aromatic heterocycle | 1583-1554-1505 cm⁻¹ |

EXAMPLE 3

11beta-[4-[5-[(2-furanylmethyl)thio]pentyloxy]phenyl]estra-1,3,5(10)-triene-3,17beta-diol Stage A: 11beta-[4-[(5-chloro-pentyl)oxy]phenyl]estra-4,9-diene-3,17-dione A solution containing: 28.2 g of 11beta-(4-hydroxyphenyl)estra-4,9-diene-3,17-dione (obtained in the preparation of Example 43 of the Patent Application EP 384842), 450 cm³ of acetone, 45 cm³ of 2N soda and 18.5 cm³ of 1-bromo-5-chloropentane is heated for 6 hours under agitation. The acetone is evaporated off and the residue is taken up in 200 cm³ of methylene chloride, washed with water, dried and concentrated to a volume of 100 cm³, 10 cm³ of isopropyl ether is added and concentration is carried out until crystallization starts, followed by separating, drying and 26.3 g of product is collected which is chromatographed on silica (eluant essence G-ethyl acetate 1/1). 4.2 g of expected product is obtained (M.p.=220° C.).

| I.R. Spectrum: CHCl₃ | |
| --- | --- |
| 17 keto | 1735 cm⁻¹ |
| 3 keto | 1658 cm⁻¹ |
| C═C and aromatic | 1609-1580-1509 cm⁻¹ |

Stage B: 3-acetyloxy 11beta-[4-[(5-chloro-pentyl)oxy]phenyl]estra-1,3,5(10)-trien-17-one 30 cm³ of acetic anhydride and 15 cm³ of acetyl bromide are added to a solution cooled down to +4° C. containing 30 g of the product obtained in the preceding stage, in 300 cm³ of methylene chloride. The reaction medium is left to return to ambient temperature, agitated for one hour, then 30 cm³ of methanol and 500 cm³ of a saturated solution of sodium bicarbonate are added while cooling down. Agitation is carried out for 45 minutes at ambient temperature, followed by decanting, washing with water, drying then evaporating to dryness. 37 g of product is obtained which is used as it is for the following stage.

Stage C: 3-hydroxy 11beta-[4-[(5-chloro-pentyl)oxy]phenyl]estra-1,3,5(10)-trien-17-one A solution containing 37 g of the product obtained in the preceding stage, 200 cm³ of tetrahydrofuran and 64 cm³ of 2N soda is agitated for 40 minutes at ambient temperature. 64 cm³ of 2N hydrochloric acid is added and the solvents are evaporated off under reduced pressure, followed by extracting with methylene chloride, washing with water, drying and bringing to dryness under reduced pressure. 32 g of desired product is obtained which is used as it is for the following stage.

Stage D: 11beta-[4-[(5-chloro-pentyl)oxy]phenyl]estra-1,3,5(10)-triene-3,17beta-diol 150 cm³ of methanol and, at 0+5° C. over 10 minutes, 2.56 g of boron and sodium hydride (at 95%) are added to a solution containing 32 g of the product obtained in the preceding stage in 150 cm³ of tetrahydrofuran. The reaction medium is agitated for 1 hour at 0+5° C. and 10 cm³ of acetone is added, the solvents are distilled off, the residue is taken up with methylene chloride, washed with water, dried and evaporated to dryness. 34 g of product is obtained which is chromatographed on silica (eluant toluene-ethyl acetate 8/2). 15.15 g of expected product is collected (M.p.=165° C. recrystallized from ethyl acetate).

I.R. Spectrum: (Nujol) absorption NH/OH region aromatic 1618-1608-1582-1512-1492 cm⁻¹

Stage E: 11beta-[4-[5-[(2-furanylmethyl)thio]pentyloxy]phenyl]estra-1,3,5(10)-triene-3,17beta-diol A mixture containing 0.15 cm³ of furfuryl mercaptan (at 90–95%), 81 mg of sodium methylate, 90 mg of sodium iodide, 4 cm³ of methanol and 234 mg of the product obtained in the preceding stage is agitated under reflux for 4 hours. The methanol is distilled off under reduced pressure, the residue is taken up in ethyl acetate, washed with water, dried and distilled to dryness under reduced pressure. 340 mg of product is obtained which is chromatographed on silica (eluant essence G-ethyl acetate 6-4). 260 mg of product is collected which is chromatographed on Lichrosorb RP18 (eluant methanol-water 9-1). In this way 140 mg of the desired product is obtained.

| I.R. Spectrum: (CHCl₃) | |
| --- | --- |
| OH | 3602 cm⁻¹ |
| aromatic + conjugated system | 1610-1581-1512-1504 cm⁻¹ |

EXAMPLE 4

11beta-[4-[5-[(2-pyridinylmethyl)thio]pentyloxy]phenyl]estra-1,3,5(10)-triene-3,17beta-diol A solution containing 0.17 cm³ of 2-pyridine methanethiol, 81 mg of sodium methylate, 234 mg of the product obtained in Stage D of Example 3 and 4 cm³ of methanol is heated for 3 hours under reflux. The methanol is distilled off, the residue is taken up with ethyl acetate, washed with water, dried and brought to dryness under reduced pressure. 360 mg of residue is collected which is chromatographed on silica (eluant ethyl acetate-essence G 8/2) and in this way 280 mg of expected product is obtained.

| I.R. Spectrum: (CHCl$_3$) | |
|---|---|
| OH | 3605 cm$^{-1}$ |
| aromatic | 1610-1581-1511 cm$^{-1}$ |
| pyridine | 1594-1571 cm$^{-1}$ |

EXAMPLE 5

11beta-[4-[5-[(2-pyridinylmethyl)sulphinyl]-pentyloxy]phenyl]estra-1,3,5(10)-triene-3,17beta-diol 3.7 cm$^3$ of a 0.1M solution of sodium metaperiodate in water is added to a solution of 172 mg of the product obtained in Example 4 in 12 cm$^3$ of methanol. The reaction medium is agitated for 1 hour 30 minutes and 3.4 cm$^3$ of methanol and 0.6 cm$^3$ of the metaperiodate solution are added, after 3 hours 30 minutes of agitation the reaction medium is poured into water, extracted with ethyl acetate, washed with salt water and evaporated to dryness under reduced pressure. 176 mg of residue is obtained which is chromatographed on silica twice (eluant methylene chloride-methanol (92.5-7.5)). 107 mg of desired product is collected.

| I.R. Spectrum: (CHCl$_3$ on Nicolet) | |
|---|---|
| OH | 3605 cm$^{-1}$ |
| heterocycle and aromatic | 1610-1596-1583-1572-1512 cm$^{-1}$ |
| sulphoxide | ≈1031 cm$^{-1}$ |

EXAMPLE 6

11beta-[4-[5-[(3-pyridinylmethyl)thio]pentyloxy]phenyl]estra-1,3,5(10)-triene-3,17beta-diol Stage A: (11beta, 11'beta)11,11'-[dithiobis-[5,1-pentoxy-(4,1-phenylene)]]di-estra-1,3,5(10)-triene-3,17beta-diol 1.9 g of 11beta-[4-[(5-chloro-pentyl)oxy]phenyl]estra-1,3,5(10)-triene-3,17beta-diol obtained in Stage D of Example 3 and 910 mg of potassium thioacetate in 20 cm$^3$ of ethanol are agitated under reflux for 17 hours. 910 mg of potassium thioacetate is added and agitation is carried out for 10 hours under reflux. The ethanol is distilled off, the residue is taken up in ethyl acetate, washed with salt water, dried and evaporated to dryness under reduced pressure. 2.1 g of residue is obtained which is chromatographed on silica (eluant: ethyl acetate-essence G 6/4), in this way 1.72 g of desired product is collected.

| I.R. Spectrum: (nujol) absorption NH/OH region | |
|---|---|
| aromatic | 1609-1580-1510 cm$^{-1}$ |

Stage B: 11beta-[4-[5-[(3-pyridinylmethyl)thio]pentyloxy]phenyl]estra-1,3,5(10)-triene-3,17beta-diol a) reduction of the disulphide:

465 mg of the product obtained in the preceding stage and 0.25 cm$^3$ of tributylphosphine are introduced into a solution of 5 cm$^3$ of methanol with 10% water and 2 cm$^3$ of tetrahydrofuran, which has been degassed beforehand. The reaction medium is agitated for 2 hours at ambient temperature, extraction is carried out with ethyl acetate, followed by washing with water, drying and evaporating to dryness under reduced pressure. 640 mg of mercaptan is obtained.

b) alkylation:

The mercaptan obtained is dissolved in 5 cm$^3$ of methanol and 160 mg of sodium methylate and 342 mg of (3-chloromethyl)pyridine hydrochloride at 96% are added.

This suspension is agitated for 55 minutes under reflux, taken to ambient temperature, acidified with 2 cm$^3$ of 2N hydrochloric acid, alkalinized with sodium bicarbonate, extracted with ethyl acetate, washed with salt water, dried and evaporated to dryness under reduced pressure. 650 mg of product is collected which is chromatographed on silica (eluant ethyl acetate-essence G 8/2). 370 mg of desired product is obtained.

| I.R. Spectrum: CHCl$_3$ | |
|---|---|
| OH | 3607 cm$^{-1}$ |
| aromatic | 1610-1580-1512 cm$^{-1}$ |

EXAMPLE 7

11beta-[4-[5-[(3-pyridinylmethyl)sulphinyl]pentyloxy]phenyl]estra-1,3,5(10)-triene-3,17beta-diol The operation is carried out as in Example 5 starting with 177 mg of the product obtained in Example 6. 185 mg of crude product is obtained to which 24 mg from a previous lot is added and the whole is chromatographed on silica twice (eluant methylene chloride-methanol 9/1). 138 mg of desired product is collected.

| I.R. Spectrum: (CHCl$_3$ on Nicolet) | |
|---|---|
| OH | 3606 cm$^{-1}$ + general absorption |
| aromatic + heteroaromatic | 1610-1580-1512 cm$^{-1}$ |
| sulphoxide approx. | 1030-1040 cm$^{-1}$ |

EXAMPLE 8

11beta-[4-[6-[(4,4,5,5,5-pentafluoro pentyl)thio]hexyloxy]phenyl]estra-1,3,5(10)-triene-3,17beta-diol Stage A: 11beta-[4-[(6-chloro hexyl)oxy]phenyl]estra-4,9-diene-3,17-dione 362 mg of 11beta-(4-hydroxy-phenyl)estra-4,9-diene-3,17-dione (obtained in the preparation of Example 43 of the Patent Application EP 384842), 5 cm$^3$ of acetone, 1.5 cm$^3$ of 6-bromo-chloro hexane and 138 mg of potassium carbonate are agitated for 5 hours under reflux. Then 1 cm$^3$ of 6-bromo-chloro hexane is added and agitation is carried out for 16 hours while leaving the temperature to return to ambient. The reaction medium is acidified with 2N hydrochloric acid, extracted with ethyl acetate, washed with water, dried and evaporated to dryness under reduced pressure. 3.48 g of product is collected which is chromatographed on silica (eluant ethyl acetate-essence G 6/4). The residue obtained is recrystallized from a methylene choride-isopropyl ether mixture and in this way 290 mg of desired product is obtained (M.p.=221° C.).

Stage B: 3-hydroxy 11beta-[4-[(6-chloro hexyl)oxy]phenyl] estra-1,3,5(10)-trien-17-one The operation is carried out as in Stages B and C of Example 3 starting with 481 mg of the product obtained in Stage A above using 0.5 cm³ of acetic anhydride and 0.25 cm³ of acetyl bromide. 483 mg of desired product is obtained.

Stage C: 11beta-[4-[(6-chloro hexyl)oxy]phenyl]estra-1,3,5(10)-triene-3,17beta-diol The operation is carried out as in Stage D of Example 3 starting with 465 mg of the product obtained above, using 60 mg of boron and sodium hydride. After chromatography on silica (eluant essence G-ethyl acetate 6/4) and recrystallization from methylene chloride, 300 mg of desired product is obtained (M.p.=176° C.).

Stage D: 11beta-[4-[(6-iodo hexyl)oxy]phenyl]estra-1,3,5(10)-triene-3,17beta-diol 150 mg of sodium iodide is added to a solution of 310 mg of the product obtained in Stage C in 6 cm³ of methylethylketone and agitation is carried out for 24 hours under reflux. 100 mg of sodium iodide is added, followed by agitation for 2 hours under reflux and for 16 hours while leaving the temperature to return to ambient, taking up in ethyl acetate, washing, drying and evaporating to dryness under reduced pressure. 470 mg of expected product is collected which is used as it is for the following stage.

Stage E: 11beta-[4-[[6-(thioacetyl)hexyl]oxy]phenyl]estra-1,3,5(10)-triene-3,17beta-diol 150 mg of potassium thioacetate is added to a solution of 470 mg of the product obtained in Stage D in 6 cm³ of ethanol and agitation is carried out for 1 hour 50 minutes at 50° C. The ethanol is distilled off, the residue is taken up in ethyl acetate, washed with water, dried and evaporated to dryness under reduced pressure. 400 mg of residue is obtained which is chromatographed on silica (eluant ethyl acetate-essence G 6/4 then 8/2). 265 mg of desired product is collected (M.p. #90° C.).

| I.R. Spectrum: CHCl₃ on Nicolet | |
|---|---|
| OH | 3602 cm⁻¹ |
| C=O | 1686 cm⁻¹ |
| aromatic | 1610-1581-1512 cm⁻¹ |

Stage F: 11beta-[4-[6-[(4,4,5,5,5-pentafluoro pentyl)thio]hexyloxy]phenyl]estra-1,3,5(10)-triene-3,17beta-diol 0.1 cm³ of caustic soda lye is added to a solution of 200 mg of the product obtained above and 127 mg of 4,4,5,5,5-pentafluoroiodopentane (whose preparation is given hereafter) in 5 cm³ of methanol. The reaction medium is agitated for 1 hour at 50° C. then the solvent is evaporated off under reduced pressure. The residue is taken up in methylene chloride and 2N hydrochloric acid, followed by extraction with methylene chloride, washing with water, drying and evaporating to dryness under reduced pressure. The residue obtained is chromatographed on silica (eluant essence G-ethyl acetate 65/35). 149 mg of desired product is obtained.

| I.R. Spectrum: CHCl₃ | |
|---|---|
| OH | 3600 cm⁻¹ |
| aromatic | 1620-1580-1512 cm⁻¹ |

PREPARATION OF EXAMPLE 8

4,4,5,5,5-pentafluoro iodopentane

Stage A: 4,4,5,5,5-pentafluoro pentanol 10 g of 4,4,5,5,5-pentafluoro-2-penten-1-ol (obtained according to J. Am. Chem. Soc., 107, (1985), 5186–5191: T. Kitazume and N. Ishikawa) is dissolved in 100 cm³ of methanol, and hydrogenation is carried out in the presence of 0.5 g of Raney nickel. The catalyst is filtered, followed by washing with ethanol and after distillation at ordinary pressure, the expected alcohol is collected B.p.: 133° C.

$n_D^{23}$: 1.3305

Stage B: 4,4,5,5,5-pentafluoro iodopentane 2.54 g of iodine and, while maintaining the temperature below 25° C., a solution of 1.78 g of the product obtained in Stage A in 3 cm³ of methylene chloride are added to a solution of 2.65 g of triphenylphosphine and 0.69 g of imidazole in 20 cm³ of methylene chloride. Agitation is carried out for 3 hours, followed by filtering, distilling the methylene chloride and taking the residue up in pentane, several times. After distillation of the pentane, 3.45 g of residue is obtained containing the expected product which can be distilled (B.p. 42–45° C. under 40 mb).

$n_D^{23}$: 1.4054

EXAMPLE 9

11beta-[4-[6-[(4,4,5,5,5-pentafluoro pentyl)sulphinyl]hexyloxy]phenyl]estra-1,3,5(10)-triene-3,17beta-diol 0.61 cm³ of a 0.5M solution of sodium metaperiodate in water is added to a solution of 110 mg of the product obtained in Example 8 in 5.5 cm³ of methanol. The reaction medium is agitated for 1 hour at ambient temperature and the methanol is evaporated off under reduced pressure. The residue is taken up in 2N hydrochloric acid and extracted with methylene chloride. After drying and evaporating to dryness of the solvent, the residue is chromatographed on silica (eluant methylene chloride-methanol 95/5). 96 mg of desired product is obtained.

| I.R. Spectrum: CHCl₃ | |
|---|---|
| OH | 3605 cm⁻¹ + associated |
| aromatic | 1610-1580-1512 cm⁻¹ |
| sulphoxide | 1031 cm⁻¹ |

EXAMPLE 9a

11beta-[4-[6-[(4,4,5,5,5-pentafluoro pentyl)sulphonyl]hexyloxy]phenyl]estra-1,3,5(10)-triene-3,17beta-diol 150 mg of perphthalic acid at 70% is added to a solution of 150 mg of the product obtained in Example 8 in 2 cm³ of methylene chloride. The reaction medium is agitated for 1 hour 15 minutes then an aqueous solution of sodium thiosulphate and an aqueous solution of sodium bicarbonate are added. Extraction is carried out with methylene chloride, followed by drying and evaporating to dryness under reduced pressure. The residue obtained is chromatographed on silica (eluant ethyl acetate-essence G 6/4). 130 mg of desired product is obtained.

| I.R. Spectrum: CHCl$_3$ | |
|---|---|
| OH | 3603 cm$^{-1}$ + associated |
| aromatic | 1622-1610-1570-1511-1505 cm$^{-1}$ |
| sulphone | 1305-1132 cm$^{-1}$ |

EXAMPLES 10 TO 13

By following the preparation method of Example 1, starting with the product obtained in Stage D of Example 1, the compound of Example 10 is prepared; by following the preparation method of Example 1 but starting with the corresponding diacetates of the compounds of formula (II), the compounds as defined above in which Hal represents a chlorine atom (Example 11) or a tosylate group (Examples 12 and 13), using for each example the mercaptan of formula (III) in which Za has the value given for Z in Table I, or its sodium salt, then by saponifying with soda the diacetate obtained in order to obtain the expected diol of formula (I), the compounds of Examples 11 to 13 are prepared.

The compounds of Examples 10 to 13 correspond to the compounds of formula (I) in which $R_{17}$ represents a hydroxyl, $R'_{17}$ represents a hydrogen atom, m has the value 0, X, Y and Z have the values given in Table I hereafter.

The IR spectra of the products of Examples 10 to 13 are given in Table I.

The products corresponding to Examples 10 to 13 of formula (I) in which m has the value 1 are prepared by following the method of Example 5.

TABLE I

| Examples | X | Y | Z | IRcm$^{-1}$ |
|---|---|---|---|---|
| 10 | CH$_2$ | (CH$_2$)$_7$ | 2-ethyl-furan | 3602(OH), 1609, 1585, 1501 |

TABLE I-continued

| Examples | X | Y | Z | IRcm$^{-1}$ |
|---|---|---|---|---|
| 11 | CH$_2$ | (CH$_2$)$_9$ | 2-thiazoline | 3603(OH), 1609, 1561, 1498 |
| 12 | CH$_2$ | (CH$_2$)$_9$ | 2-thiazole | 3602(OH), 1615, 1609, 1583, 1498 |
| 13 | CH$_2$ | (CH$_2$)$_9$ | 1,4-dimethyl-tetrazole | 3603(OH), 1609, 1580, 1500 |

EXAMPLES 14 TO 24

By following the preparation method of Example 2, the compounds of Examples 14 to 21 are prepared and by following the preparation method of Example 2 but by starting with the corresponding compounds of formula (II), the compounds of Examples 22 to 24 are prepared, compounds of formula (I) in which $R_{17}$ represents a hydroxyl, $R'_{17}$ represents a hydrogen atom, m has the value 0, X, Y and Z have the values given in Table II below, by using for each example the mercaptan of formula (III) in which Za has the value given for Z in Table II.

The IR spectra of the products of Examples 14 to 24 are given in Table II.

The products corresponding to Examples 14 to 24 of formula (I) in which m has the value 1 are prepared by following the method of Example 5.

TABLE II

| Examples | X | Y | Z | IR cm$^{-1}$ |
|---|---|---|---|---|
| 14 | Φ | C≡C—(CH$_2$) | 1,3-dimethyl-triazole | OH, NH, 2218(C≡C), 1612, 1575, 1508, 1499 |
| 15 | Φ | C≡C—(CH$_2$) | 2-methyl-4,6-diamino-pyrimidine | OH, NH 1614, 1580, 1543, 1500 |
| 16 | Φ | C≡C—(CH$_2$) | 3,5,6-trichloro-4-methyl-pyridine | 3601(OH), 1605, 1583, 1555, 1504 |

TABLE II-continued

| Examples | X | Y | Z | IR cm$^{-1}$ |
|---|---|---|---|---|
| 17 | Φ | C≡C—(CH$_2$) | 4-methyl-7-(trifluoromethyl)quinoline | 3601(OH), 2212(C≡C), 1609, 1571, 1505 |
| 18 | Φ | C≡C—(CH$_2$) | methyl 2-methylbenzoate | 3600, 3330(OH), 1705(C=O), 1617, 1603, 1585, 1575, 1560, 1505 |
| 19 | Φ | C≡C—(CH$_2$) | 2-methylbenzothiazole | 3601(OH), 2212(C≡C), 1610, 11584, 1555, 1505 |
| 20 | Φ | C≡C—(CH$_2$) | 2-ethylpyridine | 3602(OH), 1607, 1593, 1571, 1554, 1505 |
| 21 | Φ | C≡C—(CH$_2$) | 2-ethylpyran | OH, NH, 1601, 1504 |
| 22 | Φ | C≡C—(CH$_2$)$_4$ | 4-methyl-7-(trifluoromethyl)quinoline | 3604(OH), 1613, 1571, 1505 |
| 23 | Φ | C≡C—(CH$_2$)$_6$ | 4-methyl-7-(trifluoromethyl)quinoline | 3605(OH), 1615, 1610, 1571, 1505 |
| 24 | Φ | C≡C—(CH$_2$)$_6$ | 2-ethylpyridine | 3600(OH), 1609, 1596, 1571, 1505 |

EXAMPLES 25 TO 29

By following the preparation method of Example 6, the compounds of Examples 25 to 27 are prepared, by following the preparation method of Example 8 the compound of Example 28 is prepared, compounds of formula (I) in which $R_{17}$ represents a hydroxyl, $R'_{17}$ represents a hydrogen atom, m has the value 0, X, Y and Z have the values given in Table III below, by using for each example the compound of formula (VI) in which Za has the value given for Z in Table III.

The compounds corresponding to Examples 25 to 28 of formula (I) in which m has the value 1 are prepared by following the method of Example 5. Example 29 is prepared according to this method starting with the compound of Example 25.

The IR spectra of the products of Examples 25 to 29 are given in Table III.

TABLE III

| Examples | X | Y | Z | IR cm⁻¹ |
|---|---|---|---|---|
| 25 | ΦO | (CH₂)₅ | 4-ethyl-2,6-dihydroxypyrimidine | OH, NH<br>1708, 1660(C=O),<br>1608, 1578, 1510 |
| 26 | ΦO | (CH₂)₅ | 2-ethylbenzimidazole | OH, NH<br>1610, 1580, 1530, 1510 |
| 27 | ΦO | (CH₂)₅ | 8-ethyl-1,3,7-trimethylxanthine | 3608(OH),<br>1705, 1658(C=O),<br>1609, 1578, 1551,<br>1512, 1503 |
| 28 | ΦO | (CH₂)₅ | 4-ethylpyridine | 3606(OH),<br>1609, 1581, 1565, 1512<br>1609, 1585, 1501 |
| 29 | ΦO | (CH₂)₅ | 4-ethyl-2,6-dihydroxypyrimidine | OH, NH<br>1708, 1660(C=O), 1608,<br>1578, 1510, 1015(SO) |

EXAMPLE 30

11beta-[4-[5-[(4,4,5,5,5-pentafluoropentyl)thio]
pentyloxy]phenyl]estra-1,3,5(10)-triene-3,17beta-
diol By following the preparation method of Example 8, but by reacting in Stage 5-bromochloropentane on 11beta-(4-hydroxy phenyl)estra-4,9-diene-3,17-dione, the desired product is obtained.

| I.R. Spectrum: CHCl₃ on Nicolet | |
|---|---|
| C=O | absence |
| OH: | 3600 cm⁻¹ |
| Aromatic: | 1625, 1613, 1570, 1511, 1500 cm⁻¹. |

EXAMPLE 31

11beta-[4-[5-[(4,4,5,5,5-pentafluoropentyl)sulphinyl]
pentyloxy]phenyl]estra-1,3,5(10)-triene-3,17beta-
diol By following the preparation method of Example 9 and by starting with the product of Example 30, the sought compound is prepared.

| IR Spectrum: CHCl₃ on Nicolet. | |
|---|---|
| OH: | 3606 cm⁻¹ + Associated |
| Aromatic: | 1622, 1610, 1570, 1511, 1505 cm⁻¹ |
| Sulphoxide: | 1030 cm⁻¹ |

EXAMPLE 32

11beta-[4-[5-[(4,4,5,5,5-pentafluoropentyl)
sulphonyl]pentyloxy]phenyl]estra-1,3,5(10)-triene-3,
17beta-diol By following the preparation method of Example 9a starting with 225 mg of the product of Example 30, 206 mg of expected product were obtained.

| IR Spectrum: CHCl₃ | |
|---|---|
| OH: | 3604 cm⁻¹ + Associated |
| Aromatic: | 1622 (sh), 1610, 1570, 1512 cm⁻¹ |
| SO₂: | 1306, 1132 cm⁻¹ |

EXAMPLE 33

11beta-[4-(5-(pentylthio)pentyloxy)phenyl]estra-1,3,
5(10)-triene-3,17beta-diol 465 mg of the product obtained in Stage A of Example 6 and 0.25 cm³ of tributylphosphine are introduced into a solution of 5 cm³ of methanol with 10% water and 2 cm³ of tetrahydrofuran which has been degassed beforehand. The reaction medium is agitated for 1 hour at ambient temperature, 245 μl of iodopentane and 0.3 cm³ of concentrated soda are added. Agitation is carried out for 1 hour at 50° C., followed by diluting with ethyl acetate, acidifying using N hydrochloric acid, extraction with ethyl acetate, washing with salt water, drying and evaporating the solvent. After chromatographing the residue on silica (eluant:

Essence G-ethyl acetate 70-30), 570 mg of expected product is obtained.

| IR Spectrum: CHCl₃. | |
|---|---|
| OH: | 3600 cm⁻¹ |
| Aromatic: | 1610, 1582, 1511 cm⁻¹ |

EXAMPLE 34

11beta-[4-[5-[[7-(trifluoromethyl)4-quinolinyl]thio] pentyloxy]phenyl]estra-1,3,5(10)-triene-3,17beta-diol 400 mg of the chlorinated derivative obtained in Stage D of Example 3, 300 mg of 4-mercapto 7-trifluoromethyl quinoline and 68 mg of sodium methylate are mixed together at 95° C. for 43 hours. The solvent is evaporated off under reduced pressure, the residue is taken up in methylene chloride with 5% of methanol, the solution is washed with 2N hydrochloric acid, dried and the solvent is evaporated off. After chromatographing on silica (eluant: ethyl acetate-essence G-triethylamine 70-30-1 then ethyl acetate-triethylamine 99-1), 391 mg of expected product is collected which is purified by chromatographing again on silica (eluant: methylene chloride-methanol 97-3).

| IR Spectrum: CHCl₃. | |
|---|---|
| OH: | 3600 cm⁻¹ |
| Aromatic: | 1610, 1582, 1512, 1505 cm⁻¹ |
| heterocycle: | 1571, 1328, 1287, 1135, 1068 cm⁻¹ |

EXAMPLE 35

11beta-[4-[4-[(4,4,5,5,5-pentafluoropentyl)thio] butyloxy]phenyl]estra-1,3,5(10)-triene-3,17beta-diol The operation is carried out as in Stage F of Example 8 starting with 262 mg of 4,4,5,5,5-pentafluoroiodopentane prepared in Example 8 and 410 mg of the thioacetate prepared below. 335 mg of expected product is obtained.

| IR Spectrum: CHCl₃. | |
|---|---|
| OH: | 3600 cm⁻¹ |
| Aromatic: | 1610, 1581, 1512 cm⁻¹ |
| C₂F₅: | probable |

Preparation of 11beta-[4-[[4-(acetylthio)butyl]oxy] phenyl estra-1,3,5(10)-triene 3,17beta-diol used in Example 35

Stage A: 11beta [4-[(4-chlorobutyl)oxy]phenyl]estra-4,9-diene-3,17-dione

The operation is carried out as in Example 8 Stage A starting with 11beta-(4-hydroxyphenyl)estra-4,9-diene-3,17-dione (obtained in the preparation of Example 43 of the Patent Application EP 384842) and 1.04 cm³ of 1-bromo 4-chlorobutane. 630 mg of expected product is obtained.
M.p.=194° C.

Stage B: 3-hydroxy 11beta-[4-[(4-chlorobutyl)oxy]phenyl] estra-1,3,5(10)-trien-17-one The operation is carried out as in Stages B and C of Example 3 starting with 1.35 mg of the product obtained in Stage A above using 1.4 cm³ of acetic anhydride and 0.7 cm³ of acetyl bromide. 1.48 g of desired product is obtained.

Stage C: 11beta-[4-[(46-chlorobutyl)oxy]phenyl]estra-1,3,5 (10)-triene-3,17beta-diol The operation is carried out as in Stage D of Example 3 starting with 1.48 g of the product obtained above, using 60 mg boron and sodium hydride. After chromatographing on silica (eluant essence G-ethyl acetate 6/4) and recrystallization from isopropyl ether, 955 mg of the desired product is obtained. M.p.=194° C.

Stage D: 11beta-[4-[(4-iodobutyl)oxy]phenyl]estra-1,3,5 (10)-triene-3,17beta-diol The operation is carried out as in Stage D of Example 8 starting with 890 mg of the above product 600 mg of sodium iodide and 10 cm³ of methylethylketone. 1.18 g of expected product is obtained.

Stage E: 11beta-[4-[[4-(thioacetyl)butyl]oxy]phenyl]estra-1, 3,5(10)-triene-3,17beta-diol The operation is carried out as in Stage E of Example 8 starting with 1.18 g of the product obtained in Stage D and 460 mg of potassium thioacetate. 850 mg of expected product is obtained. M.p. #90° C.

EXAMPLE 36

11beta-[4-[4-[(4,4,4-trifluoropentyl)thio]butyloxy] phenyl]estra-1,3,5(10)-triene-3,17beta-diol The operation is carried out as in Stage F of Example 8 starting with 317 mg of 4,4,4-trifluoro 1-iodobutane and 410 mg of the thioacetate obtained as indicated in Preparation 35. 335 mg of expected product is obtained.

| I.R. Spectrum: CHCl₃ | |
|---|---|
| OH: | 3615 cm⁻¹ |
| aromatic: | 1610, 1579, 1512, 1501 cm⁻¹ |

EXAMPLE 37

11beta-[4-[5-[(4,4,4-trifluorobutyl)thio]pentyloxy] phenyl]estra-1,3,5(10)-triene-3,17beta-diol The operation is carried out as in Stage F of Example 8 starting with 393 mg of 4,4,4-trifluoro 1-iodobutane and 784 mg of the thioacetate obtained during the Preparation of Example 28. 640 mg of expected product is obtained.

| I.R. Spectrum: CHCl₃ | |
|---|---|
| OH: | 3601 cm⁻¹ |
| aromatic: | 1610, 1580, 1512 cm⁻¹ |

EXAMPLE 38

11beta-[4-[6-[(4,4,4-trifluorobutyl)thio]hexyloxy] phenyl]estra-1,3,5(10)-triene-3,17beta-diol The operation is carried out as in Stage F of Example 8 starting with 262 mg of 4,4,4-trifluoro 1-iodobutane and 523 mg of the thioacetate obtained in Example 8 Stage E. 380 mg of expected product is obtained.

| I.R. Spectrum: CHCl$_3$ | |
|---|---|
| OH: | 3602 cm$^{-1}$ |
| aromatic: | 1610, 1580, 1512 cm$^{-1}$ |

EXAMPLE 39

11beta-[9-[(4,4,5,5,5-pentafluoropentyl)thio]nonyl] estra-1,3,5(10)-triene-3,17beta-diol 446 mg of triphenylphosphine is dissolved in 2 cm$^3$ of methylene chloride, cooled down to 10° C., 116 mg of imidazole is added, agitation is carried out for 15 minutes, 431 mg of iodine is added, agitation is carried out for 30 minutes, 0.21 cm$^3$ of 4,4,5,5,5-pentafluoro 2-penten 1-ol is added, agitation is carried out for 4 hours at ambient temperature, the organic phase is washed with a saturated aqueous solution of sodium thiosulphate and a chloromethylenic solution of 4,4,5,5,5-pentafluoro iodopentane is obtained which is used as it is in the continuation of the synthesis. The operation is carried out as indicated in Example 8 Stage F, starting with 618 mg of the thioacetate prepared below in 7 cm$^3$ of methanol and the chloromethylenic solution of the iodated derivative prepared above. 1.2 g of expected product is obtained.

| I.R. Spectrum: CHCl$_3$ | |
|---|---|
| OH: | 3601 cm$^{-1}$ |
| aromatic: | 1609, 1585, 1501 cm$^{-1}$ |
| CF$_2$–CF$_3$: | probable |

Preparation of 11beta-[9-(acetylthio)nonyl]estra-1,3,5(10)-triene-3,17beta-diol of Example 39
Stage A: [(9-bromononyl)oxy]dimethyl[(1,1-dimethyl) ethyl]silane
443.5 g of bromononanol in 2090 cm$^3$ of methylene chloride, 314 cm$^3$ of triethylamine and 4.58 g of dimethylaminopyridine are cooled down to 0° C. 318 g of terbutyldimethylsilyl chloride dissolved in 586 cm$^3$ of methylene chloride is added over 25 minutes. Agitation is carried out for 17 hours, followed by filtering, evaporating the solvent, taking the residue up in hexane, washing with an aqueous solution of 0.1N hydrochloric acid then with salt water. The solvent is evaporated off and 620 g of crude product is obtained which is distilled and 570 g of pure product is collected (B.p.: 110–°130° C. under 0.15 to 0.20 mbars).
Stage B: 11beta-(9-hydroxynonyl)estra-4,9-diene-3,17-dione
5.2 cm$^3$ of a solution of magnesium compound (0.42 M/l) prepared from the product obtained in Stage A and 2.3 cm$^3$ of tetrahydrofuran is cooled down to 0°/+2° C. 30 mg of copper chloride is added, agitation is carried out for 30 minutes, followed by cooling down to −30° C. and 330 mg of 3-ethylenedioxy 5 (10-epoxy estr-9(11)-ene-17-one dissolved in 2 cm$^3$ of tetrahydrofuran is added and agitation is carried out for 45 minutes. 6 cm$^3$ of 2M hydrochloric acid is added and agitation is carried out for 2 hours at ambient temperature. The reaction medium is poured into a saturated aqueous solution of sodium bicarbonate, followed by extraction with ethyl acetate, washing with salt water, drying and evaporating the solvent. After chromatographing the residue on silica (eluant: ethyl acetate-cyclohexane 6-4), 192 mg of expected product is obtained.
Stage C: 11beta-[9-(4-methylbenzenesulphonyloxy)nonyl] estra-4,9-diene-3,17-dione
13.35 g of the product prepared as indicated in Stage B, 65 cm$^3$ of pyridine, 12.33 g of tosyl chloride and 0.573 g of dimethylaminopyridine are agitated for 1 hour and 30 minutes. the reaction medium is poured into water, extracted with ethyl acetate, washed with salt water, dried, the solvent is evaporated off, the residue is chromatographed on silica (eluant: ethyl acetate-cyclohexane 4-6) and 11.79 g of expected product is obtained.
Stage D: 3-hydroxy 11beta-[9-(4-methylbenzenesulphonyloxy)nonyl]estra-1,3,5(10)-triene-17-one
The operation is carried out as indicated in Stages B and C of Example 3, starting with 11.09 g of the dienone obtained in Stage C above. 9.6 g of crude product is obtained which is purified by chromatography on silica (eluant: ethyl acetate-cyclohexane 3-7). 9.48 g of expected product is obtained.
Stage E: 11beta-[9-(4-methylbenzenesulphonyloxy)nonyl] estra-1,3,5(10)-triene-3,17beta-diol
The operation is carried out as in Stage D of Example 3 starting with 889 mg of the product obtained in Stage D above and 890 mg of expected product is obtained.
Stage F: 11beta-[9-(acetylthio)nonyl]estra-1,3,5(10)-triene-3,17beta-diol
The operation is carried out as in Stage E of Example 8 starting with 1 g of the product obtained as in Stage E above and 402 mg of potassium thioacetate. After chromatography on silica (eluant: ethyl acetate-cyclohexane 3-7)636 mg of expected product is obtained.

| I.R. Spectrum: CHCl$_3$ | |
|---|---|
| OH: | 3602 cm$^{-1}$ |
| aromatic: | 1610, 1584, 1499 cm$^{-1}$ |

EXAMPLE 40

11beta-[4-[2-[2-[(4,4,5,5,5-pentafluoropentyl)thio] ethoxy]ethoxy]phenyl]estra-1,3,5(10)-triene-3,17-beta-diol.

The operation is carried out as in Stage F of Example 8 starting with 194 mg of 4,4,5,5,5-pentafluoroiodopentane prepared in Example 8 and 313 mg of the thioacetate prepared below. 330 mg of expected product is obtained.

| I.R. Spectrum: CHCl$_3$ | |
|---|---|
| OH: | 3600 cm$^{-1}$ |
| aromatic: | 1610, 1584, 1512 cm$^{-1}$ |

Preparation of 11beta-[4-[2-[2-(acetylthio)ethoxy]ethoxy] phenyl]estra-1,3,5(10)-triene-3,17beta-diol
Stage A: 2-[2-[[(1,1-dimethylethyl)dimethylsilyl]oxy] ethoxy]ethanol
20 g of diethyleneglycol is added to 9.05 g of sodium hydride in 320 cm$^3$ of tetrahydrofuran, the reaction medium is agitated for 45 minutes, 28.3 g of dimethylterbutylsilane chloride is added, agitation is carried out for 3 hours while leaving the temperature to return to ambient. Extraction is carried out with ether, followed by washing with an aqueous solution of sodium bicarbonate, with salt water, drying and evaporating the solvent. 40.25 g of expected product is obtained.

Stage B: [2-(2-bromoethoxy)ethoxy](1,1-dimethylethyl) dimethylsilane 18.2 g of carbon tetrabromide is added over 15 minutes at −15°/−20° C. to a mixture containing 11.2 g of the product of Stage A and 14.4 g of triphenylphosphine in 100 cm$^3$ of methylene chloride. Agitation is carried out for 1 hour 15 minutes at −15° C., the solvent is evaporated off, followed by taking up in pentane, agitating at ambient temperature, separating, washing with pentane and drying at 50° C. under reduced pressure. 10.1 g of expected product is obtained.

(B.p.: 58° C./0.04 mbar).

Stage C: 11beta-[4-[2-[2-[[(1,1-dimethylethyl) dimethylsilyl]oxy]ethoxy]ethoxy]phenyl]estra-4,9-diene-3, 17-dione 412 mg of the product obtained in Stage B in solution in 2 cm$^3$ of dimethylformamide is added to 362 mg of a mixture containing 362 mg of 11beta-(4-hydroxyphenyl)4, 9-estra-diene-3,17-dione, 4 cm$^3$ of dimethylformamide and 55 mg of sodium hydride. Agitation is carried out for 3 hours at ambient temperature, an aqueous solution of ammonium chloride is added, followed by extraction with ethyl acetate, washing with salt water, drying and evaporating the solvent. After chromatography on silica (eluant: ethyl acetate-essence G 6-4), 400 mg of expected product is obtained.

Stage D: 11beta-[4-[2-(2-hydroxyethoxy)ethoxy]phenyl] estra-4,9-diene-3,17-dione 1.3 cm$^3$ of 2N hydrochloric acid is added to 740 mg of the product prepared as in Stage C in solution in 8 cm$^3$ of methanol. Agitation is carried out for 1 hour, the solvent is evaporated off, followed by taking up in ethyl acetate, washing with an aqueous solution of sodium bicarbonate, with salt water, drying and evaporating the solvent. 595 mg of expected product is obtained.

Stage E: 11beta-[4-[2-[2-[(4-methylbenzenesulphonyl)oxy] ethoxy]ethoxy]phenyl]estra-4,9-diene-3,17-dione 320 mg of tosyl chloride and 70 mg of dimethylaminopyridine are added to 690 mg of the product obtained in Stage D in 5 cm$^3$ of pyridine, then two lots of 115 mg of tosyl chloride is added again. Agitation is carried out for 2 hours and 30 minutes, followed by acidifying with 6N hydrochloric acid, extraction with ethyl acetate, washing with an aqueous solution of sodium bicarbonate, with salt water, drying and evaporating the solvent under reduced pressure, the residue is chromatographed on silica (eluant: ethyl acetate-essence G 7-3 then ethyl acetate). 710 mg of expected product is obtained.

Stage F: 3-hydroxy 11beta-[4-[2-[2-[(4-methylbenzenesulphonyl)oxy]ethoxy]ethoxy]phenyl]estra-1,3,5(10)-triene-17-one The operation is carried out as indicated in Stages B and C of Example 3, starting with 705 mg of the dienone obtained in Stage E above. 785 mg of expected product is obtained.

Stage G: 11beta-[4-[2-[2-[(4-methylbenzenesulphonyl)oxy] ethoxy]ethoxy]phenyl]estra-1,3,5(10)-triene-3,17beta-diol The operation is carried out as in Stage D of Example 3 starting with 785 mg of the product obtained in Stage F above and 434 mg of expected product is obtained after chromatographing on silica (eluant: ethyl acetate-essence G 6-4).

Stage H: 11beta-[4-[2-[2-(acetylthio)ethoxy]ethoxy]phenyl] estra-1,3,5(10)-triene-3,17beta-diol The operation is carried out as in Stage E of Example 8 starting with 432 mg of the product obtained as in Stage G above and 163 mg of potassium thioacetate. After chromatography on silica (eluant: ethyl acetate-essence G 6-4)325 mg of expected product is obtained.

| IR Spectrum (CHCl$_3$) | |
|---|---|
| OH: | 3601 cm$^{-1}$ |
| S-C=O: | 1689 cm$^3$ |
| aromatic: | 1610, 1583, 1512 cm$^{-1}$ |

EXAMPLE 41

11beta-[4-[5-[(3,3,4,4,4-pentafluorobutyl)thio] pentyloxy]phenyl]estra-1,3,5(10)-triene-3,17beta-diol 589 mg of the mercaptan obtained as in Example 6 Stage Ba, 790 mg of 3,3,4,4,4-pentafluoroiodobutane (prepared as indicated for the pentafluoroiodopentane in Example 8), 820 mg of cesium carbonate and 6 cm$^3$ of dimethylformamide are mixed together. The reaction medium is heated for 1 hour at 50° C., cooled down to ambient temperature, acidified using 2N hydrochloric acid, extracted with ethyl acetate, washed with salt water and the solvent is evaporated off. After chromatographing on silica (eluant: essence G-ethyl acetate 6-4), 360 mg of expected product is obtained.

| IR Spectrum (CHCl$_3$) | |
|---|---|
| OH: | 3600 cm$^{-1}$ |
| aromatic: | 1610, 1582, 1512 cm$^{-1}$ |

EXAMPLE 42

11beta-[4-[6-[(3,3,4,4,4-pentafluorobutyl)thio] hexyloxy]phenyl]estra-1,3,5(10)-triene-3,17beta-diol The operation is carried out as in Example 41 starting with 540 mg of the appropriate mercaptan (prepared as indicated in Example 6) 700 mg of iodated reagent and 730 mg of cesium carbonate. 247 mg of expected product is obtained.

| IR Spectrum (CHCl$_3$) | |
|---|---|
| OH: | 3608 cm$^{-1}$ |
| aromatic: | 1610, 1580, 1512, 1503 (sh.) cm$^{-1}$ |

By operating as in Example 9 using at the start the appropriate diol containing a suphurated chain in position 11 and sodium metaperiodate, the products of Examples 43 to 53 were prepared.

EXAMPLE 43

3,7-dihydro 7-[2-[[5-[4-(3,17beta-dihydroxy estra-1,3,5(10)-trien-11beta-yl)phenoxy]pentyl]sulphinyl]ethyl]1,3-dimethyl 1H-purine-2,6-dione

| IR Spectrum (CHCl$_3$) | |
|---|---|
| OH: | 3605 cm$^{-1}$ |
| C=O: | 1704, 1657 cm$^{-1}$ |
| Conjugated system + aromatic: | 1608, 1581, 1551, 1512 cm$^{-1}$ |
| S → O | ≅1031 cm$^{-1}$ |

EXAMPLE 44

11beta-[4-[6-[(4,4,4-trifluorobutyl)sulphinyl]hexyloxy]phenyl]estra-1,3,5(10)-triene-3,17beta-diol

| IR Spectrum (CHCl$_3$) | |
|---|---|
| OH | ≅3604 cm$^{-1}$ |
| aromatic: | 1610, 1581, 1512 cm$^{-1}$ |
| S → O | ≅1031 cm$^{-1}$ |

EXAMPLE 45

11beta-[4-[5-[(4,4,4-trifluorobutyl)sulphinyl]pentyloxy]phenyl]estra-1,3,5(10)-triene-3,17beta-diol

| IR Spectrum (CHCl$_3$) | |
|---|---|
| OH | ≅3607 cm$^{-1}$ |
| aromatic: | 1610, 1580, 1512 cm$^{-1}$ |
| S → O | ≅1030 cm$^{-1}$ |

EXAMPLE 46

11beta-[4-[6-[(2,2,2-trifluoroethyl)sulphinyl]hexyloxy]phenyl]estra-1,3,5(10)-triene-3,17beta-diol

| IR Spectrum (CHCl$_3$) | |
|---|---|
| OH | ≅3602 cm$^{-1}$ + associated |
| aromatic: | 1610, 1581, 1512 cm$^{-1}$ |
| S → O | ≅1044 cm$^{-1}$ |

EXAMPLE 47

11beta-[4-[4-[(4,4,4-trifluorobutyl)sulphinyl]butyloxy]phenyl]estra-1,3,5(10)-triene-3,17beta-diol

| IR Spectrum (CHCl$_3$) | |
|---|---|
| OH | ≅3603 cm$^{-1}$ |
| aromatic: | 1610, 1581, 1512 cm$^{-1}$ |
| S → O | ≅1030 cm$^{-1}$ |

EXAMPLE 48

11beta-[4-[4-[(4,4,5,5,5-pentafluoropentyl)sulphinyl]butyloxy]phenyl]estra-1,3,5(10)-triene-3,17beta-diol

| IR Spectrum (CHCl$_3$) | |
|---|---|
| OH | ≅3598 cm$^{-1}$ |
| aromatic: | 1610, 1584, 1512 cm$^{-1}$ |
| S → O | ≅1031 cm$^{-1}$ |

EXAMPLE 49

11beta-[4-[5-(pentylsulphinyl)pentyloxy]phenyl]estra-1,3,5(10)-triene-3,17beta-diol

| IR Spectrum (CHCl$_3$) | |
|---|---|
| OH | ≈3605 cm$^{-1}$ |
| aromatic: | 1610, 1581, 1512 cm$^{-1}$ |
| S → O | ≈1020 cm$^{-1}$ |

EXAMPLE 50

11beta-[9-[(4,4,5,5,5-pentafluoropentyl)sulphinyl]nonyl]estra-1,3,5(10)-triene-3,17beta-diol

| IR Spectrum (CHCl$_3$) | |
|---|---|
| OH | ≈3598 cm$^{-1}$ |
| aromatic: | 1614, 1608, 1580, 1499 cm$^{-1}$ |
| S → O | ≈1020 cm$^{-1}$ |

EXAMPLE 51

11beta-[4-[5-[(3,3,4,4,4-pentafluorobutyl)sulphinyl]pentyloxy]phenyl]estra-1,3,5(10)-triene-3,17beta-diol

| IR Spectrum (CHCl$_3$) | |
|---|---|
| OH | ≈3596 cm$^{-1}$ |
| aromatic: | 1610, 1580, 1512 cm$^{-1}$ |

EXAMPLE 52

11beta-[4-[6-[(3,3,4,4,4-pentafluorobutyl)sulphinyl]hexyloxy]phenyl]estra-1,3,5(10)-triene-3,17beta-diol

| IR Spectrum (CHCl$_3$) | |
|---|---|
| OH | ≈3505 cm$^{-1}$ |
| aromatic: | 1610, 1580, 1512 cm$^{-1}$ |
| S → O | ≈1043 cm$^{-1}$ |

EXAMPLE 53

11beta-[4-[2-[2-[(4,4,5,5,5-pentafluoropentyl)sulphinyl]ethoxy]ethoxy]phenyl]estra-1,3,5(10)-triene-3,17beta-diol

| IR Spectrum (CHCl$_3$) | |
|---|---|
| OH | ≅3606 cm$^{-1}$ |
| aromatic: | 1610, 1580, 1512 cm$^{-1}$ |
| S → O | ≅1044 cm$^{-1}$ |

By operating as in Example 9a starting with 183 mg of the product prepared as indicated in Example 34 and 172 mg of perphthalic acid, the product of Examples 54 and 55 were prepared.

EXAMPLE 54

11beta-[4-[5-[(7-(trifluoromethyl)4-quinolinyl]sulphinyl]pentyloxy]phenyl]estra-1,3,5(10)-triene-3,17beta-diol

| IR Spectrum (CHCl$_3$) | |
|---|---|
| OH | ≅3602 cm$^{-1}$ + associated |
| aromatic + heterocycle: | 1610, 1583, 1511 cm$^{-1}$ |
| S → O | ≅1056 cm$^{-1}$ |

EXAMPLE 55

11beta-[4-[5-[(7-(trifluoromethyl)4-quinolinyl]sulphonyl]pentyloxy]phenyl]estra-1,3,5(10)-triene-3,17beta-diol

| IR Spectrum (CHCl$_3$) | |
|---|---|
| OH | ≅3604 cm$^{-1}$ + associated |
| aromatic + heterocycle: | 1610, 1583, 1511 cm$^{-1}$ |
| SO$_2$ | ≅1336 (sh.) and 1160 cm$^{-1}$ |

EXAMPLE 56

11beta-[4-[5-[(4,4,4-trifluorobutyl)sulphonyl]pentyloxy]phenyl]estra-1,3,5(10)-triene-3,17beta-diol 255 mg of metachloro perbenzoic acid is added to 250 mg of the diol prepared as in Example 37 in 6 cm$^3$ of methylene chloride cooled down to +4° C. The reaction medium is agitated for 45 minutes, sodium thiosulphate is added then a solution of sodium bicarbonate is added, followed by decanting, evaporating the solvent, chromatographing the residue on silica (eluant: ethyl acetate-essence G 6-4) and 210 mg of expected product is obtained.

| IR Spectrum (CHCl$_3$) | |
|---|---|
| OH | ≅3604 cm$^{-1}$ |
| aromatic: | 1610, 1580, 1512 cm$^{-1}$ |
| SO$_2$: | 1309 and ≅1136 cm$^{-1}$ |

By operating as in Example 56 using at the start the appropriate diol containing a sulphurated chain in position 11 and metachloro perbenzoic acid, the products of Examples 57 to 67 were prepared.

EXAMPLE 57

11beta-[4-[6-[(4,4,4-trifluorobutyl)sulphonyl]hexyloxy]phenyl]estra-1,3,5(10)-triene-3,17beta-diol

| IR Spectrum (CHCl$_3$) | |
|---|---|
| OH | ≅3602 cm$^{-1}$ |
| aromatic: | 1610, 1581, 1512 cm$^{-1}$ |
| SO$_2$: | ≅1306 and ≅1135 cm$^{-1}$ |

EXAMPLE 58

11beta-[4-[4-[(4,4,5,5,5-pentafluoropentyl)sulphonyl]butyloxy]phenyl]estra-1,3,5(10)-triene-3,17beta-diol

| IR Spectrum (CHCl$_3$) | |
|---|---|
| OH | ≅3605 cm$^{-1}$ |
| aromatic: | 1610, 1582, 1512 cm$^{-1}$ |
| SO$_2$: | 1305 and ≅1132 cm$^{-1}$ |

EXAMPLE 59

11beta-[4-[4-[(4,4,4-trifluorobutyl)sulphonyl]butyloxy]phenyl]estra-1,3,5(10)-triene-3,17beta-diol

| IR Spectrum (CHCl$_3$) OH/NH complex absorption | |
|---|---|
| aromatic: | 1610, 1580, 1511 cm$^{-1}$ |
| SO$_2$: | 1296 and 1134 cm$^{-1}$ |

EXAMPLE 60

11beta-[4-[4-(pentylsulphonyl)pentyloxy]phenyl]estra-1,3,5(10)-triene-3,17beta-diol

| IR Spectrum (CHCl$_3$) | |
|---|---|
| OH: | 3600 cm$^{-1}$ |
| aromatic: | 1610, 1584, 1512 cm$^{-1}$ |
| SO$_2$: | 1297 and 1130 cm$^{-1}$ |

EXAMPLE 61

11beta-[9-[(4,4,5,5,5-pentafluoropentyl)sulphonyl]nonyl]estra-1,3,5(10)-triene-3,17beta-diol

| IR Spectrum (CHCl$_3$) | |
|---|---|
| OH: | 3601 cm$^{-1}$ |
| aromatic: | 1609, 1584, 1500 cm$^{-1}$ |
| SO$_2$: | 1309 and 1134 cm$^{-1}$ |

EXAMPLE 62

11beta-[4-[5-[(3,3,4,4,4-pentafluorobutyl)sulphonyl]pentyloxy]phenyl]estra-1,3,5(10)-triene-3,17beta-diol

| IR Spectrum (CHCl$_3$) | |
|---|---|
| OH: | 3596 cm$^{-1}$ |
| aromatic: | 1610, 1580, 1512 cm$^{-1}$ |

EXAMPLE 63

11beta-[4-[6-[(3,3,4,4,4-pentafluorobutyl)sulphonyl]hexyloxy]phenyl]estra-1,3,5(10)-triene-3,17beta-diol

| IR Spectrum (CHCl$_3$) | |
|---|---|
| OH: | 3600 cm$^{-1}$ |
| aromatic: | 1610, 1580, 1512, 1504 cm$^{-1}$ |
| SO$_2$: | 1298 and 1134 cm$^{-1}$ |

EXAMPLE 64

11beta-[4-[2-[2-[(4,4,5,5,5-pentafluoropentyl)sulphonyl]ethoxy]ethoxy]phenyl]estra-1,3,5(10)-triene-3,17beta-diol

| IR Spectrum (CHCl$_3$) | |
|---|---|
| OH: | 3600 cm$^{-1}$ |
| aromatic: | 1610, 1580, 1512 cm$^{-1}$ |
| SO$_2$: | 1317 and 1129 cm$^{-1}$ |

EXAMPLE 65

11beta-[4-[5-[(7-(trifluoromethyl)4-quinolinyl]sulphinyl]pentyloxy]phenyl]estra-1,3,5(10)-triene-3,17beta-diol This product is identical to that obtained in Example 54.

| IR Spectrum (CHCl$_3$) | |
|---|---|
| OH: | ≃3602 cm$^{-1}$ + associated |
| aromatic: | 1610, 1583, 1511 cm$^{-1}$ |
| S → 0 | ≃1056 cm$^{-1}$ |

EXAMPLE 66

3-hydroxy 11beta-[4-[5-[(4,4,5,5,5-pentafluoropentyl)sulphinyl]pentyloxy]phenyl]estra-1,3,5(10)-triene-17beta-yl and sodium butanedioate a) Preparation of the acid 380 mg of the product obtained in Example 31, 355 mg of succinic anhydride, 40 mg of dimethylaminopyridine and 4 cm$^3$ of pyridine are agitated for 4 hours at 120° C. The reaction medium is left to return to ambient temperature, 4 cm$^3$ of methanol, 4 cm$^3$ of water and 650 mg of potassium carbonate are added. Agitation is carried out for 6 hours 30 minutes, followed by cooling down to +4° C., acidifying using hydrochloric acid, extracting with ethyl acetate, washing with salt water, drying and evaporating the solvents. After chromatographing on silica (eluant: essence G-acetone 5-5), 400 mg of the acid is obtained.

| IR Spectrum (CHCl$_3$) | |
|---|---|
| OH | ≃3600 cm$^{-1}$ + general absorption of OH acid type |
| C=O: | 1717 cm$^{-1}$ + complex |
| aromatic: | 1610, 1585, 1512 cm$^{-1}$ | b) Salification 367 mg of the acid obtained above is dissolved in 4 cm$^3$ of ethanol, 36 mg of sodium bicarbonate dissolved in 4 cm$^3$ of water is added, agitation is carried out for 30 minutes, the ethanol is evaporated off, 20 cm$^3$ of water is added, followed by filtering then lyophilizing. 250 mg of expected product is collected.

EXAMPLE 67

3-hydroxy 11beta-[4-[5-[(4,4,5,5,5-pentafluoropentyl)sulphonyl]pentyloxy]phenyl]estra-1,3,5(10)-triene-17beta-yl and sodium butanedioate The operation is carried out as in Example 66 starting with 290 mg of the product obtained in Example 32, 285 mg of product is obtained in the form of the acid.

| IR Spectrum (CHCl$_3$) | |
|---|---|
| OH: | 3598, 3518 cm$^{-1}$ + general absorption |
| C=O: | 1716 cm$^{-1}$ |
| aromatic: | 1610, 1582, 1512 cm$^{-1}$ |
| SO$_2$: | 1304, 1133 cm$^{-1}$ |

273 mg of the acid is salified and 235 mg of expected crude product is obtained which is purified by chromatographing on silica (eluant: methanol-water 8-2).

EXAMPLE 68

3-cyclopentyloxy 11beta-[4-[5-[(4,4,5,5,5-pentafluoropentyl)sulphinyl]pentyloxy]phenyl]estra-1,3,5(10)-triene-17beta-ol 1 g of the product prepared in Example 31, 8.7 cm$^3$ of dimethylformamide and 82 mg of sodium hydride are agitated for 30 minutes. Then 486 mg of cyclopentyl 4-methylbenzenesulphonate is added, agitation is carried out for 5 hours, the whole is poured into an aqueous solution of ammonium chloride, extracted with ethyl acetate, washed with salt water, dried and the solvent is evaporated off. The residue is chromatographed on silica (eluant: methylene chloride-isopropanol 95-5) and 861 mg of product is obtained which is crystallized from a methylene chloride/ethyl ether mixture and 777 mg of expected product is collected.

M.p.=189° C.

| IR Spectrum (CHCl$_3$) | |
|---|---|
| OH | ≃3608 cm$^{-1}$ |
| aromatic: | 1610, 1580, 1570, 1512, 1498 cm$^{-1}$ |
| S → O | ≃1043 cm$^{-1}$ |

Preparation of cyclopentyl 4-methylbenzenesulphonate 1 g of cyclopentanol, 23 cm$^3$ of pyridine, 4.42 g of tosyl chloride and 195.8 mg of 4-dimethylaminopyridine are agitated for 3 hours at ambient temperature, the pyridine is evaporated off, the reaction medium is poured into water, extracted with ethyl acetate, washed with an aqueous solution of M hydrochloric acid then with salt water and with a saturated aqueous solution of sodium bicarbonate. The solvents are evaporated off, the residue is dissolved in methanol, sodium bicarbonate is again added, followed by evaporation, the residue is chromatographed on silica (eluant: ethyl acetate-essence G 1-9) and 1.41 g of the expected tosylate is obtained.

EXAMPLE 69

3-cyclopentyloxy 11beta-[4-[5-[(4,4,5,5,5-pentafluoropentyl)sulphonyl]pentyloxy]phenyl]estra-1,3,5(10)-triene-17beta-ol By operating as in Example 56 using at the start 698 mg of the product obtained in Example 68 and 228 mg of metachloro perbenzoic acid, 567 mg of expected product is obtained. M.p.=166° C.

| IR Spectrum (CHCl$_3$) | |
|---|---|
| OH | ≈3608 cm$^{-1}$ |
| aromatic: | 1610, 1580, 1570, 1512, 1498 cm$^{-1}$ |

EXAMPLE 70

3-cyclopentyloxy 11beta-[4-[5-[(4,4,5,5,5-pentafluoropentyl)sulphonyl]pentyloxy]phenyl]estra-1,3,5(10)-triene-17beta-yl and sodium butanedioate By operating as indicated in Example 66 starting with 384 mg of the product obtained as in Example 68, 301 mg of an acid is obtained after crystallization from a methylene chloride/isopropyl ether mixture. M.p.=188° C.

| IR Spectrum (CHCl$_3$) | |
|---|---|
| C=O: | 1716 cm$^{-1}$ |
| aromatic: | 1610, 1580, 1572, 1512, 1498 cm$^{-1}$ |

285.5 mg of the above acid is salified and 295 mg of expected product is obtained after lyophilization.

| IR Spectrum (CHCl$_3$) | |
|---|---|
| OH/NH: | general absorption |
| C=O: | 1724 cm$^{-1}$ |
| aromatic: | 1609, 1510, 1498 cm$^{-1}$ |
| COO$^-$ | ≈1578 cm$^{-1}$ |

EXAMPLE 71

3-hydroxy 11beta-[4-[5-[(4,4,5,5,5-pentafluoropentyl)thio]pentyloxy]phenyl]estra-1,3,5(10)-triene-17beta-one Stage A: 3-hydroxy 11beta-[4-[(5-iodopentyl)oxy]phenyl]estra-1,3,5(10)-triene-17-one The operation is carried out as in Stage D of Example 8 using at the start 14.9 g of the product obtained as in Example 3C. 13.2 g of expected product is obtained. Rf=0.18 (cyclohexane-ethyl acetate 7-3).

Stage B: 3-hydroxy 11beta-[4-[[5-(thioacetyl)pentyl]oxy]phenyl]estra-1,3,5(10)-triene-17-one The operation is carried out as in Stage E of Example 8 using at the start 13.2 g of the product obtained in Stage A. 9 g of expected product is obtained. Rf=0.58 (cyclohexane-ethyl acetate 7-3).

Stage C: 3-hydroxy 11beta-[4-[5-[(4,4,5,5,5-pentafluoropentyl)thio]pentyloxy]phenyl]estra-1,3,5(10)-triene-17-one The operation is carried out as in Stage F of Example 8 using at the start 9 g of the product obtained in Stage B. 8.63 g of expected product is obtained. Rf=0.6 (cyclohexane-ethyl acetate 6-4).

EXAMPLE 72

3-hydroxy 11beta-[4-[5-[(4,4,5,5,5-pentafluoropentyl)sulphinyl]pentyloxy]phenyl]estra-1,3,5(10)-triene-17-one The operation is carried out as in Example 9 using 180 mg of the product obtained in Example 71. 120 mg of expected product is obtained. Rf=0.37 (methylene chloride-ethanol 95-5).

EXAMPLE 73

3-hydroxy 11beta-[4-[5-[(4,4,5,5,5-pentafluoropentyl)sulphonyl]pentyloxy]phenyl]estra-1,3,5(10)-triene-17-one The operation is carried out as in Example 56 using at the start 180 mg of the product obtained in Example 71 and 162 mg of metachloro perbenzoic acid. 160 mg of expected product is obtained.

EXAMPLE 74

17-methylene 11beta-[4-[5-[(4,4,5,5,5-pentafluoropentyl)sulphonyl]pentyloxy]phenyl]estra-1,3,5(10)-triene-3-ol 500 mg of the product obtained in Example 73 is added to a mixture containing 815 mg of methyltriphenylphosphonium bromide, 5 cm$^3$ of dioxan and 125 mg of sodium methylate. Agitation is carried out for 16 hours at ambient temperature, 100 cm$^3$ of an aqueous solution of ammonium chloride is added, followed by extracting with methylene chloride, drying, eliminating the solvent under reduced pressure and chromatographing the residue on silica (eluant: cyclohexane-ethyl acetate 7-3). 80 mg of expected product is obtained.

| IR Spectrum (CHCl$_3$) | |
|---|---|
| Little or no C=O | |
| OH: | 3596 cm$^{-1}$ |
| C=C: | 1656 cm$^{-1}$ |
| aromatic: | 1610, 1580, 1512 cm$^{-1}$ |

EXAMPLE 75

17-beta (hydroxymethyl)11beta-[4-[5-[(4,4,5,5,5-pentafluoropentyl)sulphonyl]pentyloxy]phenyl]estra-1,3,5(10)-triene-3-ol 60 mg of the product obtained in Example 74 in 3 cm$^3$ of tetrahydrofuran is cooled down to +4° C. and 100 μl of dimethylborane sulphide is added. Agitation is carried out for 2 hours at ambient temperature, followed by cooling down to 0° C., 200 µl of caustic soda lye then 200 µl of 30% hydrogen peroxide are added. The reaction medium is left to return to ambient temperature then acidification is carried out with a hydrochloric acid solution, followed by extracting with methylene chloride, drying and eliminating the solvent. The residue is chromatographed on silica (eluant: ethyl acetate-cyclohexane 3-7) and 35 mg of expected product is obtained.

| IR Spectrum (CHCl$_3$) | |
| --- | --- |
| phenolic OH: | 3590 cm$^{-1}$ |
| aromatic: | 1610, 1580, 1511 cm$^{-1}$ |
| C=C or conjugated C=O | ≈1660 cm$^{-1}$ |

EXAMPLE 76

3-hydroxy 11beta-[4-[5-[(4,4,5,5,5-pentafluoropentyl)sulphonyl]pentyloxy]phenyl]estra-1,3,5(10)-triene-17-one oxime A mixture containing 30 cm$^3$ of ethanol and 5 cm$^3$ of water then 320 mg of hydroxylamine hydrochloride and 501 mg of sodium acetate are added to 1 g of the product obtained as in Example 73. The reaction medium is heated for 2 hours under reflux, 50 cm$^3$ of water is added, followed by extraction with methylene chloride, drying, eliminating the solvent under reduced pressure, crystallizing the residue from isopropyl ether, filtering, chromatographing the residue on silica (cyclohexane-ethyl acetate 7-3) and 90 mg of expected product is obtained.

| IR Spectrum (CHCl$_3$) | |
| --- | --- |
| OH: | 3593 cm$^{-1}$ + associated |
| aromatic: | 1610, 1582, 1512, 1502 (sh.) cm$^{-1}$ |

EXAMPLE 77

3-hydroxy 11beta-[4-[5-[(4,4,5,5,5-pentafluoropentyl)sulphonyl]pentyloxy]phenyl]estra-1,3,5(10)-triene-17-one hydrazone 100 µl of hydrazine hydrate and 3 mg of paratoluenesulphonic acid are added to 300 mg of the product obtained in Example 73 in 3 cm$^3$ of methanol. Agitation is carried out for 16 hours at ambient temperature, 50 cm$^3$ of an aqueous solution of sodium bicarbonate is added, extraction is carried out with methylene chloride, the solvent is evaporated off, the residue is chromatographed on silica (eluant: ethyl acetate) and 190 mg of expected product is obtained.

| IR Spectrum (CHCl$_3$) | |
| --- | --- |
| OH: | 3599 cm$^{-1}$ |
| NH$_2$: | 3395 cm$^{-1}$ |
| C=N and aromatic: | 1610, 1588, 1512, 1503 cm$^{-1}$ |

EXAMPLE 78

11beta-[4-[5-[(4,4,5,5,5-pentafluoropentyl) sulphonyl]pentyloxy]phenyl]17alpha-methyl estra-1,3,5(10)-triene-3,17beta-diol Heptahydrated cerium chloride is dehydrated for 2 hours at 180° C. under reduced pressure and left to cool down, 1.5 g of it is introduced into 15 cm$^3$ of tetrahydrofuran, agitation is carried out for 1 hour, 4 cm$^3$ of methyllithium in a 1.5M solution in ether is added at −60° C., agitation is carried out for 30 minutes, followed by cooling down to −78° C. and 300 mg of the product obtained in Example 71 is added. The reaction medium is maintained under agitation at −78° C. for 1 hour, an aqueous solution of ammonium chloride is added, extraction is carried out with methylene chloride, the solvent is evaporated off, the residue is chromatographed on silica (eluant: cyclohexane-ethyl acetate 7-3) and 198 mg of the 17-methylated derivative is obtained. The operation is carried out as in Example 56 starting with 198 mg of the product obtained above and 150 cm$^3$ of metachloro perbenzoic acid and 62 mg of expected product is obtained. Rf=0.37 (cyclohexane-ethyl acetate 1-1).

EXAMPLE 79

3-(cyclopentyloxy)11beta-[4-[5-[(4,4,5,5,5-pentafluoropentyl)sulphonyl]pentyloxy]phenyl]estra-1,3,5(10)-triene-17-one The operation is carried out as in Example 68 using at the start 300 mg of the product obtained in Example 71 and 170 mg of cyclopentyl 4-methyl benzene sulphonate. The reaction medium obtained is extracted with methylene chloride, dried, the solvent is evaporated off, the residue is chromatographed on silica (eluant: ethyl acetate-cyclohexane 3-7) and 290 mg of expected product is obtained which is used as it is.

EXAMPLE 80

3-(cyclopentyloxy)11beta-[4-[5-[(4,4,5,5,5-pentafluoropentyl)sulphonyl]pentyloxy]phenyl]19-nor 17alpha-pregna-1,3,5(10)-triene-20-yn-17beta-ol 150 µl of trimethylsilyl acetylene in 5 cm$^3$ of tetrahydrofuran is cooled down to −78° C. and 625 µl of a solution of n-butyllithium in hexane (1.6M) is added dropwise. Agitation is carried out for 30 minutes, 140 mg of the product obtained in Example 79 in solution in 1 cm$^3$ of tetrahydrofuran is added and agitation is carried out for 2 hours at ambient temperature. 2 cm$^3$ of a 1M solution of tetrabutylammonium fluoride in tetrahydrofuran is added. Agitation is carried out for 1 hour at ambient temperature, 10 cm$^3$ of water is added, followed by extracting with methylene chloride, drying and evaporating the solvent. After chromatographing on silica (eluant: cyclohexane-ethyl acetate 7-3), 60 mg of expected product is obtained.

EXAMPLE 81

17alpha-ethynyl 11beta-[4-[5-[(4,4,5,5,5-pentafluoropentyl)thio]pentyloxy]phenyl]estra-1,3,5(10)-triene-3,17beta-diol 126 mg of lithium acetylide in the form of a complex with ethylenediamine (Li—C≡CH.EDA) is added to 1 g of the product obtained in Example 71 in 10 cm$^3$ of tetrahydrofuran. Agitation is carried out for 2 hours, another 180 mg of (Li—C≡CH.EDA) is added and agitation is carried out for 12 hours at ambient temperature. The reaction medium is poured into a saturated solution of ammonium chloride, followed by extraction with methylene chloride, washing with an N hydrochloric acid solution, drying and eliminating the solvent. After chromatographing on silica (eluant: ethyl acetate-cyclohexane 2-8 then methylene chloride-methanol 98-2), 720 mg of expected product is obtained used as it is in the following example.

EXAMPLE 82

17alpha-ethynyl 11beta-[4-[5-[(4,4,5,5,5-pentafluoropentyl)sulphonyl]pentyloxy]phenyl]estra-1,3,5(10)-triene-3,17beta-diol The operation is carried out as in Example 56 using at the start 570 mg of the product obtained in Example 79 and 1 g of metachloro perbenzoic acid. 100 mg of expected product is obtained.

| IR Spectrum (CHCl$_3$) | |
| --- | --- |
| OH: | 3598 cm$^{-1}$ |
| C≡CH: | 3308 cm$^{-1}$ |
| aromatic: | 1610, 1580, 1510, 1502 cm$^{-1}$ |

EXAMPLE 83

11beta-[4-[5-[(nonafluorobutyl)thio]pentyloxy]phenyl]estra-1,3,5(10)-triene-3,17beta-diol 50 mg of sodium hydride is added under an inert gas atmosphere to 466 mg of the product obtained in Example 6Ba in solution in 10 cm$^3$ of dimethylformamide, agitation is carried out for 30 minutes, 0.18 cm$^3$ of perfluorobutyl iodide is added, the reaction medium is cooled down and subjected to 15 minutes of radiation from a mercury vapour lamp, followed by acidifying with 2N hydrochloric acid, extracting with ethyl acetate, washing with water, drying, evaporating the solvent, chromatographing the residue on silica (eluant: essence G-ethyl acetate 6-4 then with ethyl acetate alone, then methanol-water 9-1). 287 mg of expected product is collected. Rf=0.24.

| IR Spectrum (CHCl$_3$) | |
| --- | --- |
| OH: | 3602 cm$^{-1}$ |
| aromatic: | 1610, 1583, 1512 cm$^{-1}$ |

EXAMPLE 84

3-hydroxy 11beta-[4-[5-[(4,4,5,5,5-pentafluoropentyl)sulphonyl]pentyloxy]phenyl]16alpha-methyl estra-1,3,5(10)-triene-17-one Stage A: 3-hydroxy 11beta-[4-[5-[(4,4,5,5,5-pentafluoropentyl)thio]pentyloxy]phenyl]16alpha-methyl estra-1,3,5(10)-triene-17-one 500 mg of 3-tetrahydropyranyloxy 11beta-[4-[6-[(4,4,5,5,5-pentafluoropentyl)thio]pentyloxy]phenyl]estra-1,3,5(10)-triene-17-one is cooled down to −78° C., 750 μl of lithium nitrate trimethylsulphide is added, agitation is carried out for 10 minutes, 200 mg of methyl iodide is added, agitation is carried out for 1 hour at ambient temperature, a saturated aqueous solution of ammonium chloride is added, followed by extraction with methylene chloride, drying, evaporating the solvent, chromatographing the residue on silica (eluant: cyclohexane-ethyl acetate 8-2) and 280 mg of the 16-methylated derivative is obtained to which 5 cm$^3$ of ethanol then 2 cm$^3$ of hydrochloric acid are added, agitation is carried out for 3 hours at ambient temperature, a saturated solution of ammonium chloride is added, followed by extraction with methylene chloride, drying and evaporating the solvent. The residue is chromatographed on silica (eluant: cyclohexane-ethyl acetate 7-3). 150 mg of expected product is obtained.

Stage B: 3-hydroxy 11beta-[4-[5-[(4,4,5,5,5-pentafluoropentyl)sulphonyl]pentyloxy]phenyl]16alpha-methyl estra-1,3,5(10)-triene-17-one 100 mg of the product obtained above in 5 cm$^3$ of methylene chloride is cooled down to 0° C., 90 mg of metachloroperbenzoic acid is added, agitation is carried out for 1 hour at 0° C., an aqueous solution of sodium thiosulphate and sodium bicarbonate (1-1) is added, followed by extraction with methylene chloride, drying, and evaporating the solvent. The residue is chromatographed on silica (eluant: cyclohexane-ethyl acetate 7-3) and 60 mg of expected product is obtained.

| IR Spectrum (CHCl$_3$) | |
| --- | --- |
| C=O: | 1730 cm$^{-1}$ |
| aromatic: | 1610, 1578, 1510, 1498 cm$^{-1}$ |

Preparation of 3-tetrahydropyranyloxy 11beta-[4-[6-[(4,4,5,5,5pentafluoropentyl)thio]pentyloxy]phenyl]estra-1,3,5(10)-triene-17one 4 g of 3-hydroxy 11beta-[4-[5-[(4,4,5,5,5-pentafluoropentyl)thio]pentyloxy]phenyl]estra-1,3,5(10)-triene-17-one, 40 cm$^3$ of dioxane, 3 cm$^3$ of dihydropyran and 100 cm$^3$ of paratoluenesulphonic acid are agitated for 3 hours at ambient temperature. 100 cm$^3$ of a saturated aqueous solution of sodium bicarbonate is added, followed by extraction with methylene chloride, drying and evaporating the solvent. The residue is chromatographed on silica (eluant: cyclohexane-ethyl acetate 7-3) and 4.5 g of expected product is obtained.

By operating as in Stage D of Example 3 using the product obtained in Example 84 at the start, 11beta-[4-[5-[(4,4,5,5,5-pentafluoropentyl)sulphonyl]pentyloxy]phenyl] 16alpha-methyl estra-1,3,5(10)-triene-3,17beta-diol was prepared.

EXAMPLE 85

11beta-[4-[5-[(pentafluorophenyl)methylthio]pentyloxy]phenyl]estra-1,3,5(10)-triene-3,17beta-diol The operation is carried out as in Example 6Ba starting with 350 mg of the disulphide and 0.19 cm$^3$ of tributylphosphine. 0.12 cm$^3$ of alpha-bromo 2,3,4,5,6-pentafluorotoluene and 0.15 cm$^3$ of caustic soda lye are added to the mercaptan solution obtained. Agitation is carried out at 50° C. for 40 minutes, followed by cooling down, pouring the reaction medium into a 2N hydrochloric acid solution, extracting with ethyl acetate, drying and evaporating the solvent. The residue is chromatographed on silica (eluant: essence G-ethyl acetate 7-3) and 227 mg of expected product is obtained.

| IR Spectrum (CHCl$_3$) | |
| --- | --- |
| OH: | 3598 cm$^{-1}$ |
| aromatic: | 1654, 1610, 1580, 1520, 1506 cm$^{-1}$ |

EXAMPLE 86

11beta-[4-[5-[[(pentafluorophenyl)methyl]
sulphonyl]pentyloxy]phenyl]estra-1,3,5(10)-triene-3,
17beta-diol The operation is carried out as in Example 56 using at the start 207 mg of the product obtained in Example 85 and 169 mg of meta-chloroperbenzoic acid. 222 mg of expected product is obtained after chromatographing on silica (eluant: AcOEt-cyclohexane 5-5).

| IR Spectrum (CHCl$_3$) | |
|---|---|
| OH: | 3603 cm$^{-1}$ |
| aromatic: | 1654, 1610, 1580, 1520, 1506 cm$^{-1}$ |
| SO$_2$: | 1331, 1131 cm$^{-1}$ |

EXAMPLE 87

11beta-[4-[5-[(2-(pentafluorophenyl)ethyl]thio]
pentyloxy]phenyl]estra-1,3,5(10)-triene-3,17beta-
diol and 11beta-[4-[5-[(4-ethenyl 2,3,5,6-
tetrafluorophenyl)thio]pentyloxy]phenyl]estra-1,3,5
(10)-triene-3,17beta-diol The operation is carried out as in Example 6Ba using at the start 500 mg of the disulphide and 0.27 cm$^3$ of tri-n-butyltriphenylphosphine. The mercaptan solution obtained is treated as indicated in Example 85 using 0.30 cm$^3$ of 1-(2--bromoethyl) 2,3,4,5,6-pentafluorobenzene. 420 mg of expected product is obtained in the form of a mixture.
Preparation of 1-(2-bromoethyl)2,3,4,5,6-pentafluorobenzene
Stage A: 2-(2,3,4,5-pentafluoropheny)ethanol
2.5 g of 2,3,4,5,6-pentafluorophenyl acetic acid in 25 cm$^3$ of tetrahydrofuran is heated under reflux for 2 hours in the presence of 3.2 cm$^3$ of borohydride dimethyl sulphide complex. The reaction medium is cooled down, poured slowly into ice-cooled water, an aqueous solution of sodium bicarbonate is added, followed by extraction with ethyl acetate, washing with water, drying and evaporating the solvent. 2.24 g of expected product is obtained.
Stage B: 1-(2-bromoethyl) 2,3,4,5,6-pentafluorobenzene
2.225 g of the alcohol obtained in Stage A is dissolved in 21.5 cm$^3$ of methylene chloride, the reaction medium is cooled down to −20° C., 4.35 g of tetrabromomethane and 3.44 g of triphenylphosphine are added. Agitation is carried out for 4 hours at +4° C., the solvent is evaporated off, the residue is taken up in pentane, agitated, filtered, the insoluble part is washed with pentane, the filtrates are reunited and the solvent is evaporated off under reduced pressure. 3.22 g of expected product is obtained.

EXAMPLE 88

11beta-[4-[5-[(2-(pentafluorophenyl)ethyl]
sulphonyl]pentyloxyl phenyl]estra-1,3,5(10)-triene-
3,17beta-diol and 11beta-[4-[5-[(4-ethenyl 2,3,5,6-
1tetrafluorophenyl)sulphinyl]pentyloxy]phenyl]
estra-1,3,5(10)-triene-3,17beta-diol The operation is carried out as in Example 56 using at the start 420 mg of the mixture obtained in Example 87 and 346 mg of meta-chloroperbenzoic acid. 443 mg of expected product is obtained in the form of a mixture. After chromatographing on silica (eluant: ethyl acetate-cyclohexane 5-5 then acetone-methylene chloride 1-9), 84 mg of the pentafluorinated derivative and 201 mg of the tetrafluorinated derivative are obtained.

| IR Spectrum (CHCl$_3$) | |
|---|---|
| pentafluorinated derivative | |
| OH | ≅ 3602 cm$^{-1}$ |
| aromatic: | 1656, 1610, 1580, 1522, 1508 cm$^{-1}$ |
| SO$_2$ | ≅ 1323 cm$^{-1}$ |
| tetrafluorinated derivative | |
| OH | ≅ 3600 cm$^{-1}$ |
| C═C: | 1648 cm$^{-1}$ |
| aromatic: | 1610, 1578, 1512, 1478 cm$^{-1}$ (F.) |
| S → O | ≅ 1055 cm$^{-1}$ |

EXAMPLE 89

11beta-[4-[5-[3-(pentafluorophenyl)propyl]thio]
pentyloxy]phenyl]estra-1,3,5(10)-triene-3,17beta-
diol The operation is carried out as in Example 85 using at the start 500 mg of the disulphide obtained as in Example 6Ba then 2 cm$^3$ of chloromethylenic solution of 3-iodopropyl pentafluoro benzene. 472 mg of expected product is obtained.

| IR Spectrum (CHCl$_3$) | |
|---|---|
| OH | ≅ 3598 cm$^{-1}$ |
| aromatic: | 1655, 1610, 1580, 1521, 1512, 1504 cm$^{-1}$ |

Preparation of 3-iodopropyl pentafluoro benzene
Stage A: (2,3,4,5,6-pentafluorobenzene) propionic acid
971 mg of rhodium chloro-tris-triphenylphosphine is added to a solution containing 2.5 g of 2,3,4,5-pentafluorocinnamic acid, 34 cm$^3$ of ethanol and 34 cm$^3$ of toluene then hydrogenation (1700 mbar) is carried out for 6 hours at ambient temperature. The solvent is evaporated off, the residue is taken up in methylene chloride, extraction is carried out with a 1N aqueous soda solution, followed by washing with methylene chloride, acidifying using hydrochloric acid, extracting with methylene chloride, drying and evaporating the solvent under reduced pressure. The residue is crystallized from cyclohexane and 2.06 g of expected product is obtained.
Stage B: 3-(pentafluorophenyl)propanol
The operation is carried out as in the preparation of Example 87 Stage A using at the start 1.99 g of the acid obtained above and 2.4 cm$^3$ of borohydride-dimethylsulphide complex. 1.89 g of expected crude product is obtained which is chromatographed on silica (eluant: ethyl acetate-cyclohexane 4-6).
Stage C: 3-iodopropyl pentafluoro benzene
356 mg of triphenylphosphine in 2 cm$^3$ of methylene chloride is cooled down to +10° C., 95 mg of imidazole is added, agitation is carried out for 15 minutes, followed by cooling down to 0° C., 357 mg of iodine is added, agitation is carried out for 30 minutes while leaving the temperature to return to ambient temperature, 315 mg of the alcohol obtained in Stage B is added, agitation is carried out for 4 hours and the reaction medium is filtered. The chloromethylenic solution is washed using a 0.2N aqueous solution of sodium thiosulphate then with water and the chloromethylenic solution of the expected product is obtained which is used as it is in Example 89.

EXAMPLE 90

11beta-[4-[5-[3-(pentafluorophenyl)propyl-sulphonyl]pentyloxy]phenyl]estra-1,3,5(10)-triene-3,17beta-diol The operation is carried out as in Example 56 starting with 451 mg of the product obtained in Example 89 and 365 mg of meta-chloroperbenzoic acid. 305 mg of expected product is obtained after chromatographing on silica (eluant: ethyl acetate-cyclohexane 6-4) and crystallization from ethanol. M.p. =130° C.

| IR Spectrum (Nujol) | |
|---|---|
| complex absorption OH region | |
| aromatic: | 1659, 1610, 1580, 1522, 1510, 1501 cm$^{-1}$ |
| SO$_2$: | 1358, 1130 cm$^{-1}$ |

EXAMPLE 91

11beta-[4-[5-[[2,3,5,6-tetrafluoro-4-(trifluoromethyl)phenyl]methylthio]pentyloxy]phenyl]estra-1,3,5(10)-triene-3,17beta-diol The operation is carried out as in Example 85 using at the start 500 mg of the disulphide obtained as in Example 6Ba then 857 mg of alpha,alpha,alpha, 2,3,5,6-heptafluoro p-xylene bromide. 259 mg of expected product is obtained.

| IR Spectrum (CHCl$_3$) | |
|---|---|
| OH: | 3600 cm$^{-1}$ |
| aromatic: | 1664, 1610, 1578, 1512, 1500 cm$^{-1}$ |

Preparation of alpha,alpha,alpha, 2,3,5,6-heptafluoro p-xylene bromide.

2 g of alpha,alpha,alpha, 2,3,5,6-heptafluoro p-xylene bromide in 7.4 cm$^3$ of carbon tetrachloride is heated under reflux in the presence of 15 mg of azo isobutyronitrile and 1.53 g of N-bromosuccinimide is added over 30 minutes then reflux is maintained for 96 hours. After cooling down and filtering, the filtrate is evaporated, the residue is taken up in pentane, the solvent is evaporated off and 1.40 g of product is obtained which is used as it is in Example 91.

EXAMPLE 92

11beta-[4-[[5-[[2,3,5,6-tetrafluoro-4-(trifluoromethyl)phenyl]methyl]sulphonyl]pentyloxy]phenyl]estra-1,3,5(10)-triene-2,17beta-diol The operation is carried out as in Example 56 using at the start 241 mg of the product obtained in Example 91 and 193 mg of metachloroperbenzoic acid. 161 mg of expected product is obtained after chromatographing on silica (eluant: ethyl acetate-cyclohexane 5-5).

| IR Spectrum (CHCl$_3$) | |
|---|---|
| OH: | 3610 cm$^{-1}$ |
| aromatic: | 1622, 1611, 1578, 1511, 1504 cm$^{-1}$ |
| CF$_3$ + SO$_2$ region: | 1336 cm$^{-1}$ |

EXAMPLE 93

11beta-[9-[(4,4,5,5,5-pentafluoropentyl)sulphonyl]nonyl]estra-1,3,5(10)-triene3,17beta-diol 3,17-diacetate 3.39 g of the product obtained in Example 61 in 16.6 cm$^3$ of pyridine, 3.14 cm$^3$ of acetic anhydride and 154 mg of dimethylaminopyridine are agitated for 45 minutes at ambient temperature. 5.4 cm$^3$ of methanol is added, followed by agitation for 10 minutes, evaporating the solvents, the residue is taken up in ethyl acetate, followed by washing with an aqueous solution of M hydrochloric acid, then with sodium chloride, drying and evaporating the solvent. After chromatographing the residue on silica.(eluant: ethyl acetate-cyclohexane 5-5 then 3-7), 3.25 g of expected product is obtained.

| IR Spectrum(CHCl$_3$) | |
|---|---|
| C=O: | max. 1725 cm$^{-1}$ sh. 1746 cm$^{-1}$ |
| aromatic: | 1610, 1602, 1583, 1493 cm$^{-1}$ |
| SO$_2$: | 1309, 1134 cm$^{-1}$ |

EXAMPLE 94

11beta-[9-[(4,4,5,5,5-pentafluoropentyl)sulphonyl]nonyl]estra-1,3,5(10)-triene-3,17beta-diol 17-acetate 1.37 g of the diacetate obtained in Example 93 in 27.5 cm$^3$ of methanol with 10% water is cooled down to 0° C. and 203 mg of potassium bicarbonate is added, the reaction medium is left to return to ambient temperature and agitation is carried out for 19 hours. The reaction medium is poured into 220 cm$^3$ of water with 55 cm$^3$ of 0.1N hydrochloric acid added to it, extracted with ethyl acetate, dried and the solvent is evaporated off. The residue is chromatographed on silica (eluant: ethyl acetate-cyclohexane 35-65) then the residue is crystallized from a methylene chloride/isopropyl ether mixture. 973 mg of expected product is obtained. M.p.=130° C.

| IR Spectrum (CHCl$_3$) | |
|---|---|
| OH | ≅ 3600 cm$^{-1}$ + associated |
| OAC: | 1724, 1252 cm$^{-1}$ |
| aromatic: | 1611, 1585, 1498 cm$^{-1}$ |
| SO$_2$: | 1308, 1134 cm$^{-1}$ |

EXAMPLE 95

3-methoxy 11beta-[9-[(4,4,5,5,5-pentafluoropentyl)sulphonyl]nonyl]estra-1,3,5(10)-triene-17beta-ol acetate 2.9 cm$^3$ of water is added to 1.05 g of the phenol obtained in Example 94 in solution in 3.9 cm$^3$ of acetone, agitation is carried out, 0.3 cm$^3$ of methyl sulphate and 0.83 cm$^3$ of an 2N aqueous soda solution are added and agitation is carried out for 1 hour at ambient temperature. The reaction medium is acidified with 1 cm³ of 2N hydrochloric acid, poured into an aqueous solution of sodium bicarbonate, extracted with ethyl acetate, dried and the solvent is evaporated off. After chromatographing the residue on silica (eluant: ethyl acetate-cyclohexane 3-7), 959 mg of expected product is obtained.

| IR Spectrum (CHCl₃) | |
|---|---|
| C=O: | 1723 cm⁻¹ |
| aromatic: | 1609, 1575, 1500 cm⁻¹ |

EXAMPLE 96

11beta-[4-[5-[(4,4,5,5,5-pentafluoropentyl)thio]pentyloxy]estra-1,3,5(10)-triene-3,17beta-diol 3,17-diacetate 0.1 cm³ of concentrated sulphuric acid in solution in 2.5 cm³ of isopropenyl acetate is added to 200 mg of the product obtained in Example 71 in solution in 2.5 cm³ of isopropenyl acetate. The reaction medium is heated to 97° C., the acetone/isopropenyl acetate mixture is slowly distilled, the sulphuric acid solution is again added and distillation is carried out as previously. The residue is taken up in an aqueous solution of sodium bicarbonate and extracted with ether. After drying and evaporating the solvent 510 mg of expected product is obtained which is used as it is for the following example.

EXAMPLE 97

3-hydroxy 11beta-[4-[5-[(4,4,5,5,5-pentafluoropentyl)thio]pentyloxy]phenyl]16alpha-bromo-estra-1,3,5(10)-triene-17-one A solution containing 0.025 cm³ of bromine, 43 mg of sodium acetate and 5 cm³ of an acetic acid-water mixture (40-1) is added dropwise to the product obtained in Example 96 in solution in 3 cm³ of acetic acid. The reaction medium is agitated for 12 hours at ambient temperature, a saturated aqueous solution of sodium bicarbonate is added, followed by extraction with methylene chloride, drying, chromatographing the residue on silica (eluant: ethyl acetate-cyclohexane 3-7) and 20 mg of expected product is obtained.

EXAMPLE 98

3-hydroxy 11beta-[4-[5-[(4,4,5,5,5-pentafluoropentyl)sulphonyl]pentyloxy]phenyl]16alpha-bromo-estra-1,3,5(10)-triene-17-one The operation is carried out as in Example 56 using at the start 120 mg of the product obtained in Example 97 and 100 mg of metachloroperbenzoic acid. 38 mg of expected product is obtained.

| IR Spectrum (CHCl₃) | |
|---|---|
| C=O: | 1750 cm⁻¹ |
| OH: | 3595 cm⁻¹ |
| aromatic: | 1611, 1580, 1512, 1502 cm⁻¹ |
| SO₂: | 1305, 1133 cm⁻¹ |

EXAMPLE 99

11beta-[4-[5-[(4,4,5,5,5-pentafluoropentyl)sulphonyl]pentyloxy]phenyl]16alpha-bromo-estra-1,3,5(10)-triene-3,17beta-diol By operating as in Stage D of Example 3 starting with the product obtained in Example 98, the expected product was obtained.

Pharmaceutical Compositions

Tablets were prepared corresponding to the following formula:

| Product of Example 5 | 50 mg |
|---|---|
| Excipient (talc, starch, magnesium stearate) | 120 mg |
| s.q. for a tablet completed at | |

Pharmacological Study of the Products of the Invention

1—Study of the Activity of the Products of the Invention on the Estrogen Receptor of a Mouse Uterus 18 to 21-day old impuberal female mice are sacrificed, the uteri are removed, then homogenized at 0° C., using a Potter teflon-glass in a TS buffered solution (10 mM Tris, 0.25 M saccharose, HCl pH 7.4) (1 g of tissue per 25 ml of TS). The homogenate is then ultracentrifuged (209,000 g×30 mn.) at 0° C. The supernatant aliquots thus obtained are incubated at 25° C. for 5 hours, with a constant concentration (T) of tritiated estradiol in the presence of increasing concentrations either of unlabelled estradiol (0–1000×10⁻⁹M), or of unlabelled product to be tested (1 to 25000×10⁻⁹M). The concentration of bound tritiated estradiol (B) is then measured in each incubate by the carbon-dextran adsorption technique.

Calculation of the Relative Bond Affinity (RBA)

The following two curves are drawn: the percentage of bound tritiated hormone B/BO as a function of the logarithm of the concentration of unlabelled reference hormone or as a function of the logarothm of the concentration of unlabelled test product.

The straight line of the following equation:

$$I^{50}=100 \ (B/BO \ max+Bmin/BO)/2 \ \text{i.e.} \ I_{50}=100 \ (1+Bmin/BO)//2=50(1+Bmin/BO)$$

is determined.

BO=% of binding of the bound tritiated hormone in the absence of any unlabelled product.

B=% of the bound tritiated hormone in the presence of a concentration X of unlabelled product.

B min=% of bound tritiated hormone in the presence of a large excess of unlabelled reference hormone (500 nM).

The intersections of the straight line I₅₀ and the curves allow the evaluation of the concentrations of unlabelled reference hormone (CH) and of the unlabelled test product (CX) which inhibit by 50% the specific binding of the tritiated hormone on the receptor.

The relative bond affinity (RBA) of the test product is calculated by the equation:

| RBA = 100 (CH)/CCX). | |
|---|---|
| Products of Examples | Estrogen receptor incubation 5H at 25° C. |
| 5 | 21.2 |
| 7 | 26.3 |
| 32 | 56 |
| 60 | 18.2 |
| 78 | 21.8 |

2—Anti-proliferative Activity of the Products of the Invention on the Growth of MCF-7 Mammary Tumour Cells
Description of the Test
a) Cell Culture MCF-7 lines are kept in culture in FCS medium (according to 1) at 37° C. in a humid atmosphere containing 5% $CO_2$. Subconfluent cells are collected by trypsination (0.05% trypsin, 0.02% EDTA) then rinsed by gentle centrifugation. A sample of cells in suspension is counted with a Malassez cell.

b) Growth Study

The cells, resuspended in DSE medium (according to 1), are seeded at the rate of 50,000 cells per well in multiwell plates (24 wells of 2.5 cm²). Twenty-four hours after seeding (D0), the product to be tested is added to the medium in ethanolic solution (final concentration of ethanol: 0.1%), at a concentration of $10^{-11}$ to $10^{-6}$M, the control wells receiving the same ethanol concentration. The media are renewed every 48 hours. At the end of the experiment (D7 to D9), the medium is extracted and the cells are immediately fixed with 150 microlitres of methanol in order to dose the DNA.

The anti-proliferative activity of the products is evaluated by their capacity to inhibit the increase of DNA c) DNA Dosage The DNA is dosed by a fluorimetric method using DABA (3,5 diaminobenzoic acid) (according to 2): 150 microlitres of DABA are added to each well; the plates are then incubated for 45 mn at 56° C., then 2 ml of 1N HCl is added. The fluorescence is measured using a fluorimeter (excitation wavelength: 408 nm, emission wavelength: 510 nm).

The quantity of DNA per well is evaluated relative to a reference scale obtained by treating a calf thymus DNA standard under the same conditions.

Results

The concentration in nM which inhibits the growth of MCF7 cells by 50% ($IC_{50}$) was determined in the manner indicated above:

Results

| product of Example 1 | IC 50 = 0.024 nM |
| product of Example 5 | IC 50 = 0.012 nM |
| product of Example 7 | IC 50 = 0.026 nM |
| product of Example 32 | IC 50 = 0.1 nM |
| product of Example 60 | IC 50 = 0.25 nM |
| product of Example 78 | IC 50 = 0.03 nM |

(1) A Base Medium is Prepared as Follows
MEM medium (Minimal Essential Medium) to which are added:
  1% non-essential amino acids (GIBCO),
  peni-strepto (100 U/ml penicillin, 0.1 mg/ml streptomycin),
  0.1% fungizone,
  2 mM glutamine,
  2.25 mg/ml sodium bicarbonate.

The FCS medium is composed of 95% of base medium and 5% of foetal calf serum.

The DSE medium is composed of 95% of base medium, 5% of steroid-free foetal calf serum on carbon-dextran and $10^{-10}$ M of estradiol.

(2) Puzas and Goodman, Analytical Biochemistry, Vol 86, p. 50, 1978

What is claimed is:

1. A compound of formula

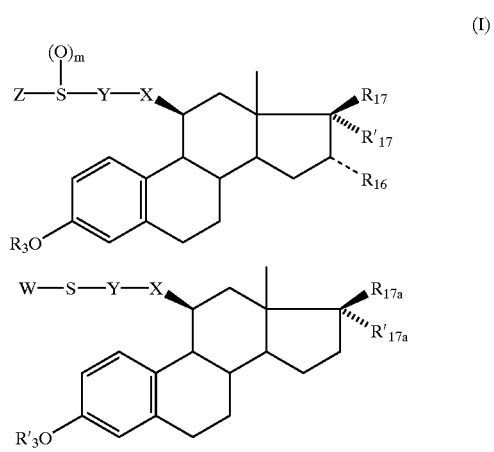

(I)

wherein $R_{17a}$ and $R'_{17a}$ taken together form a member of the group consisting of a ketone, an oxime, hydrazono and methylene or $R_{17a}$ is selected from the group consisting of protected —OH, protected hydroxymethyl and acyloxy of up to 12 carbon atoms, and $R'_{17a}$ is selected from the group consisting of hydrogen and alkyl, alkenyl and alkynyl of up to 8 carbon atoms, each optionally substituted, X is selected from the group consisting of methylene, arylene and arylenoxy group having at most 10 carbon atoms linked to the steroid by a carbon atom, Y is saturated or unsaturated, aliphatic of 1 to 18 carbon atoms, optionally interrupted by an oxygen atoms, $R'_3$ is hydrogen or a hydroxy protective group, and W is hydrogen or —COR with R being alkyl of 1 to 5 carbon atoms.

* * * * *